United States Patent [19]

Lee et al.

[11] Patent Number: 5,786,171
[45] Date of Patent: Jul. 28, 1998

[54] AORTIC PREFERENTIALLY EXPRESSED GENE AND USES THEREOF

[75] Inventors: Mu-En Lee, Newton; Chung-Ming Hsieh, Cambridge, both of Mass.

[73] Assignee: President and Fellows of Harvard University, Cambridge, Mass.

[21] Appl. No.: 494,577

[22] Filed: Jun. 22, 1995

[51] Int. Cl.$^6$ .............. C12P 21/02; C12N 5/10; C12N 15/85; C07H 21/04
[52] U.S. Cl. .............. 435/69.1; 435/70.1; 435/320.1; 435/325; 536/23.1
[58] Field of Search .............. 435/69.1, 320.1, 435/70.1, 325; 536/23.1; 424/93.21

[56] References Cited

PUBLICATIONS

Blobel et al., "Structure, Function and Evolutionary Relationship of Proteins Containing a Disintegrin Domain", *Curr. Opin. Cell Biol.*, 4:760–65 (1992).

Del Sal et al., "The Growth Arrest–Specific Gene, gas1, Is Involved in Growth Suppression", 1992, *Cell*, 70:595–607 (1992).

Gallagher et al., "The Carboxyl Terminus of the Smooth Muscle Myosin Light Chain Kinase Is Expressed as an Independent Protein, Telokin", *J. Biol. Chem.*, 266:23945–52 (1991).

Gorski et al., "Molecular Cloning of a Diverged Homeobox Gene That Is Rapidly Down–Regulated During the $G_0/G_1$ Transition in Vascular Smooth Muscle Cells", *Mol. and Cell. Biol.*, 13:3722–33 (1993).

Holden, et al., "X–ray Structure Determination of Tekokin, the C–terminal Domain of Myosin Light Chain Kianse, at 2·8 Å Resolution", *J. Mol. Biol.*, 277:840–51 (1992).

Hunter et al., "Targeting Gene Expression to Specific Cardiovascular Cell Types in Transgenic Mice", *Hypertension*, 22:608–17 (1993).

Hynes, "Integrins: Versatility, Modulation, and Signaling in Cell Adhesion", *Cell*, 69:11–25 (1992).

Kozak, "At Lease Six Nucleotides Preceding the AUG Initiator Codon Enhance Translation in Mammalian Cells", *J. Mol. Biol.*, 196:947–50 (1987).

Leco et al., "Tissue Inhibitor of Metalloproteinases–3 (TIMP–3) Is an Extracellular Matrix–associated Protein with a Distinctive Pattern of Expression in Mouse Cells and Tissues", *J. Biol. Chem.*, 269:9352–60 (1994).

Pauly et al., "Experimental Models That Mimic the Differentiation and Dedifferentiation of Vascular Cells", *Circulation (Supp III)*, 86:III–68–73 (1992).

Ross, "The Pathogenesis of Atherosclerosis: A Perspective for the 1990s", *Nature*, 362:801–809 (1993).

Ruoslahti et al., "New Perspectives in Cell Adhesion: RGD and Integrins", *Science*, 238:491–96 (1987).

Shanahan et al., "Isolation of Gene Markers of Differentiated and proliferating Vascular Smooth Muscle Cells", *Circulation Res.*, 73:193–204 (1993).

Sun et al., "Molecular Cloning of Five Messenger RNAs Differentially Expressed in Preneoplastic or Neoplastic JB6 Mouse Epidermal Cells: One Is Homologous to Human Tissue Inhibitor of Metalloproteinases–3", *Cancer Res.*, 54:1139–44.

Hsieh et al., "APEG–1, a Novel Gene Preferentially Expressed in Aortic Smooth Muscle Cells, is Down–regulated by Vascular Injury," *FASEB J*. 10:6, p. A1012, No. 74 (1996).

Hsieh et al., "APEG–1, A Novel Gene Preferentially Expressed In Aortic Smooth Muscle Cells, is Down–regulated by Vascular Injury," *J. Biol. Chem.* (Microfilms) 271(29):17354–59 (1996).

McGeoch et al., "Complete DNA Sequence of the Short Repeat Region in the Genome of Herpes Simplex Virus Type I," *Nucleic Acids Research* 14(4):1727–1745 (1986).

EMBL EST, Accession no R24327, Sequence reference yg32f04.r1, 23–APR.–1995, Homo sapiens cDNA clone 33988 5' XP002014921.

EMBL EST, Accession no W55328, Sequence reference mb12e01.r1, 06–Jun.–1996, Life Tech mouse brain, Mus musculus cDNA clone 319992 5' XP002014922.

*Primary Examiner*—Nancy Degen
*Attorney, Agent, or Firm*—Fish & Richardson P.C.

[57] ABSTRACT

An aortic-preferentially-expressed gene-1 (APEG-1) polypeptide, DNA sequences encoding and controlling the transcription of APEG-1, methods of diagnosing vascular injury, and methods of inhibiting vascular smooth muscle cell proliferation by increasing the level of APEG-1 at the site of vascular injury.

14 Claims, 13 Drawing Sheets

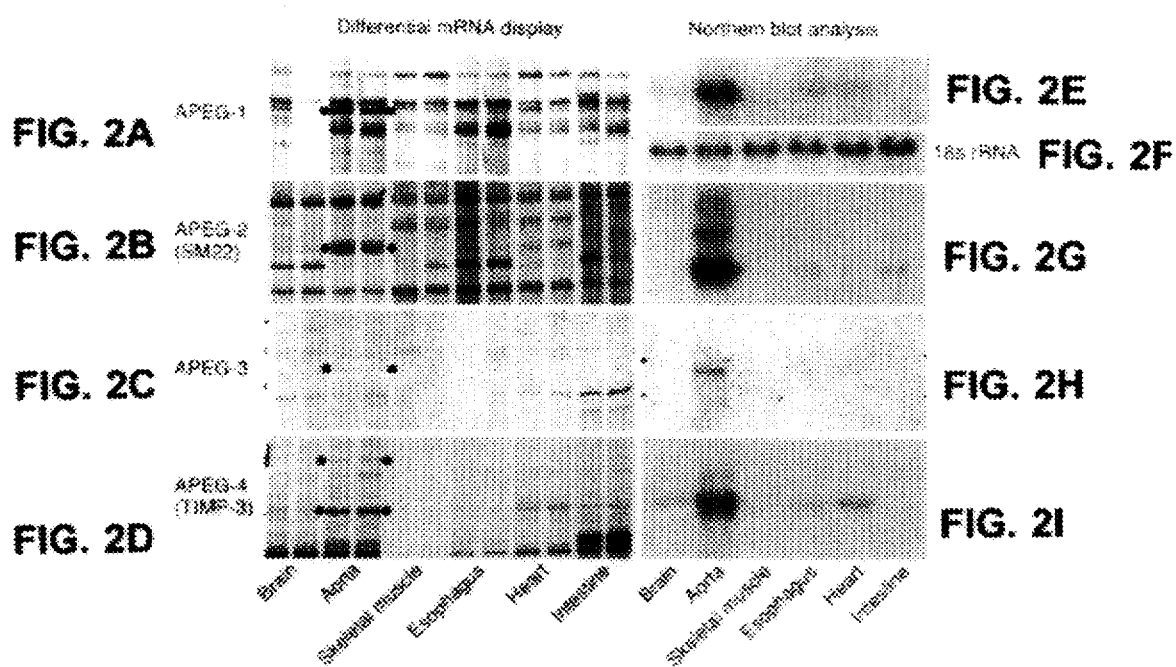

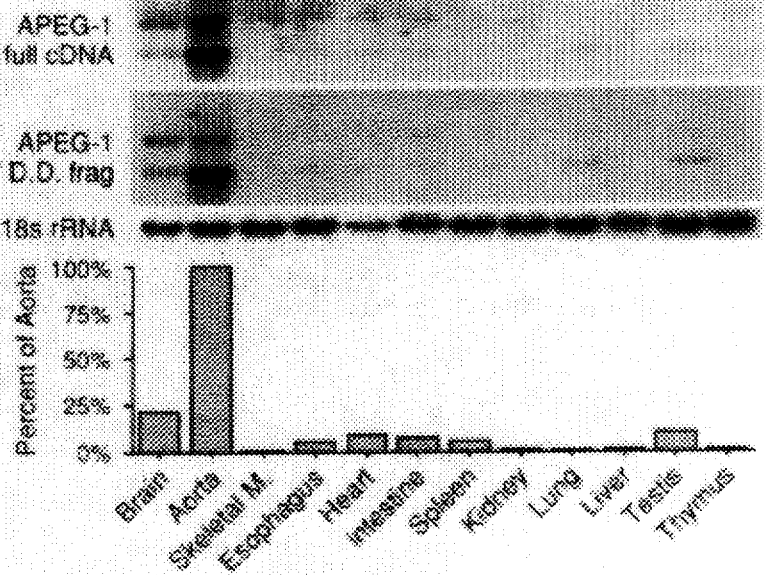
FIG. 4

FIG. 5

```
   1  gaattcggcacgagcagagacttaaggaaggtgcagacggggtccgtttgcacagcctcagggcgcgtcc
  71  acatcccccttcagcagcccaatcaccctctgatgaggagtacctgagccccccagaggagttcccagaac
 141  ctggggagacctggtcccgaaCccTACCATGAAGCCCAGTCCAGCCCAGGATCGAGATTCCTCTGACTC
 211  TTCCTCCAAGGCCACCCCCAACCTTCAAGGTCTCACTCAGTCTCATGGACCAATCAGTGAGAGAAGGTCAAGATGTC
 281  ATTATGAGCATCCGCGTGCAGGGGAGCCCAAGCCTGTCTCCTGGCTTGAGGAATCGGCAGCCTGTGC
 351  GCCCAGACCAGCGGCGCTTTGCAGAGGAGCCGAGGGTGGGCTCTGCCCGAGGTTGAGGATCCTGGCTGA
 421  GAGGGAGATGCTGGTTTCTACACTTGCAAGGCGGTCAACGAATATGGCTCGGCAGTGTGAGGCCCGC
 491  CTGGAGGTCCGAGGCGAGTGAgctcagggggccacctgcgctgcctcactgccgagctgcacccgcgg
 561  tgtctcaggcacctcctgacctcgtgtttcactgccctccctgccacagaccccggctcggccggc
 631  cccggacatagcccatgctccctccctccctagcacagcccaccctgggtaacccatcgggcccc
 701  tgtggatcctccctcccccaagtggatatggctgtgtgcagaccaggaggcccccagcgagtgtt
 771  gagaaggggatgccatgagagttgtgctacaggccactgagctcgtctgcctgtgtctgtgacagt
 841  aatgcatgtgctatgctgcaggccactgtctctgcctgtcctgcctgtgtctgtgtgacagt
 911  cagggaagaaacctTCGAGCTGaggtgggacagaacattttattccacatgagaataagactctgtgaga
 981  tgcagggcccagagggcaggcacagtggcacaacatctctgggaaggtaggcactgaccattgc
1051  agaaatgggttttaaatggcaagcttaggaccacagcttcttcacagacacatccgacacgtctgt
1121  gccctgactgctgcagagtagccagactgagcacaggagcaggtcatagtggactggagtttggaaacact
1191  ctgggaatgagagagtagcacaggtttgtacccaaaaaaaaaaaaaa
1261  atttcgtagctcaaataagtccagtttgtaccaaataagtccagt
```

SEQ ID NO:1

|   |   |   |   |   |   |   |   |   |   |   |   |   |   |   |   |   |
|---|---|---|---|---|---|---|---|---|---|---|---|---|---|---|---|---|
| 1 | ATG | AAG | CCC | AGT | CCC | AGC | CAG | GAT | CGA | GAT | TCC | TCT | GAC | TCT | TCC | AAG |
|   | Met | Lys | Pro | Ser | Pro | Ser | Gln | Asp | Arg | Asp | Ser | Ser | Asp | Ser | Ser | Lys |
| 18 | GCA | CCC | CCA | ACC | TTC | AAG | GTC | TCA | CTC | ATG | GAC | CAA | TCA | GTG | AGA | GAA | GGT |
|   | Ala | Pro | Pro | Thr | Phe | Lys | Val | Ser | Leu | Met | Asp | Gln | Ser | Val | Arg | Glu | Gly |
| 35 | CAA | GAT | GTC | ATT | ATG | AGC | ATC | CGC | GTG | CAG | GGG | GAG | CCC | AAG | CCT | GTG | GTC |
|   | Gln | Asp | Val | Ile | Met | Ser | Ile | Arg | Val | Gln | Gly | Glu | Pro | Lys | Pro | Val | Val |
| 52 | TCC | TGG | CTG | AGG | AAT | CGG | CAG | CCT | GTG | CGC | CCA | GAC | CAG | CGG | CGC | TTT | GCA |
|   | Ser | Trp | Leu | Arg | Asn | Arg | Gln | Pro | Val | Arg | Pro | Asp | Gln | Arg | Arg | Phe | Ala |
| 69 | GAG | GAG | GCC | GAG | GGT | CTC | TGC | CGG | TTG | AGG | ATC | CTG | GCT | GCT | GAG | AGG | |
|   | Glu | Glu | Ala | Glu | Gly | Leu | Cys | Arg | Leu | Arg | Ile | Leu | Ala | Ala | Glu | Arg | |
| 86 | GGA | GAT | GCT | GGT | TTC | TAC | ACT | TGC | AAG | GCG | GTC | AAC | GAA | TAT | GGC | GCT | CGG |
|   | Gly | Asp | Ala | Gly | Phe | Tyr | Thr | Cys | Lys | Ala | Val | Asn | Glu | Tyr | Gly | Ala | Arg |
| 103 | CAG | TGT | GAG | GCC | CGC | CTG | GAG | GTC | CGA | GGC | GAG | TGA |   |   |   | SEQ ID NO:2 |
|   | Gln | Cys | Glu | Ala | Arg | Leu | Glu | Val | Arg | Gly | Glu | *** |   |   |   | SEQ ID NO:3 |

FIG. 6

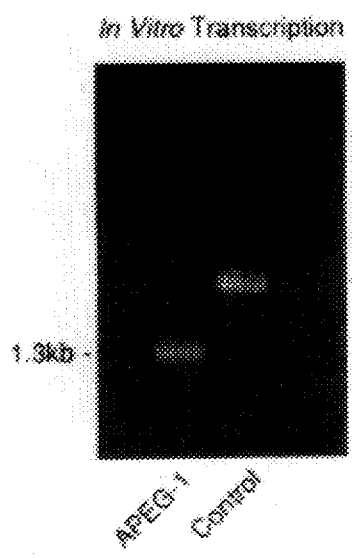 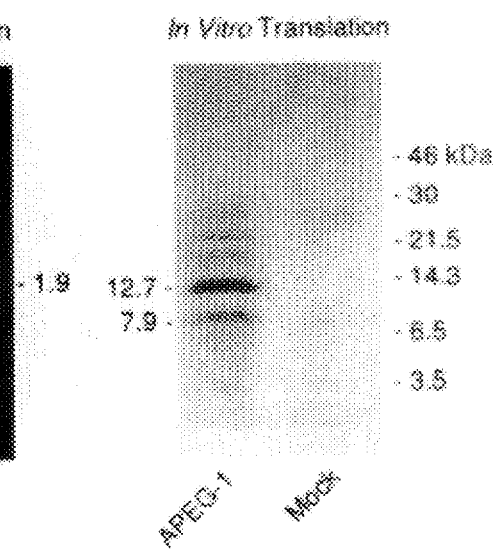
FIG. 7A  FIG. 7B

```
ChkTelo    MAMISGMSGR KASGSSPTSP INADKVENED .....AFLEEV AEEKPHVKPY FTKTILDMEV
ChkMLCK    MAMISGMSGR KASGSSPTSP INADKVENED .....AFLEEV AEEKPHVKPY FTKTILDMEV
RabTelo    MAMISGLSGR KSSTGSPTSP LTAERLETEE DVSQAFLEAV AEEKPHVKPY FSKTIRDLEV
RabMLCK    MAMISGLSGR KSSTGSPTSP LTAERLETEE DVSQAFLEAV AEEKPHVKPY FSKTIRDLEV
APEG-1     MKPSPSQDR  DSSDSSSKAP ..........  .......... ..........PT FKVSLMDQSV
Consensus  ----S----R --S---S---P ---------- ---------- ------P--- -F----D---V ChkTelo    VEGSAARFDC KIEGYPDPEV MWYKDDQPVK ESRHFQIDYD EEGNCSLTIS EVCGDDDAKY
ChkMLCK    VEGSAARFDC KIEGYPDPEV MWYKDDQPVK ESRHFQIDYD EEGNCSLTIS EVCGDDDAKY
RabTelo    VEGSAARFDC KIEGYPDPEV VWFKDDQSIR ESRHFQIDYD EDGNCSLIIS DVCGDDDAKY
RabMLCK    VEGSAARFDC KIEGYPDPEV VWFKDDQSIR ESRHFQIDYD EDGNCSLIIS DVCGDDDAKY
APEG-1     REGQDVIMSI RVQGEPKPVV SWLRNRQPVR PDQRRFAEEA EGGLCRLRIL AAERGDAGFY
Consensus  -EG------- ---------- -W-----Q-- ---------- E-G-C-L-I- -----D---Y ChkTelo    TCKAVNSLGE ATCTAELLVE TMGKEGEGEG EGEEDEEEEE  E  SEQ ID NO:4
ChkMLCK    TCKAVNSLGE ATCTAELLVE TMGKEGEGEG EGEEDEEEEE  E  SEQ ID NO:5
RabTelo    TCKAVNSLGE ATCTAELIVE TME.EGEGEG EEEEEE           SEQ ID NO:6
RabMLCK    TCKAVNSLGE ATCTAELIVE TME.EGEGEG EEEEEE           SEQ ID NO:7
APEG-1     TCKAVNEYGA RQCEARLEVR GE                         SEQ ID NO:8
Consensus  TCKAVN--G- --C-A-L-V- ---------- ------           SEQ ID NO:9
```

FIG. 8

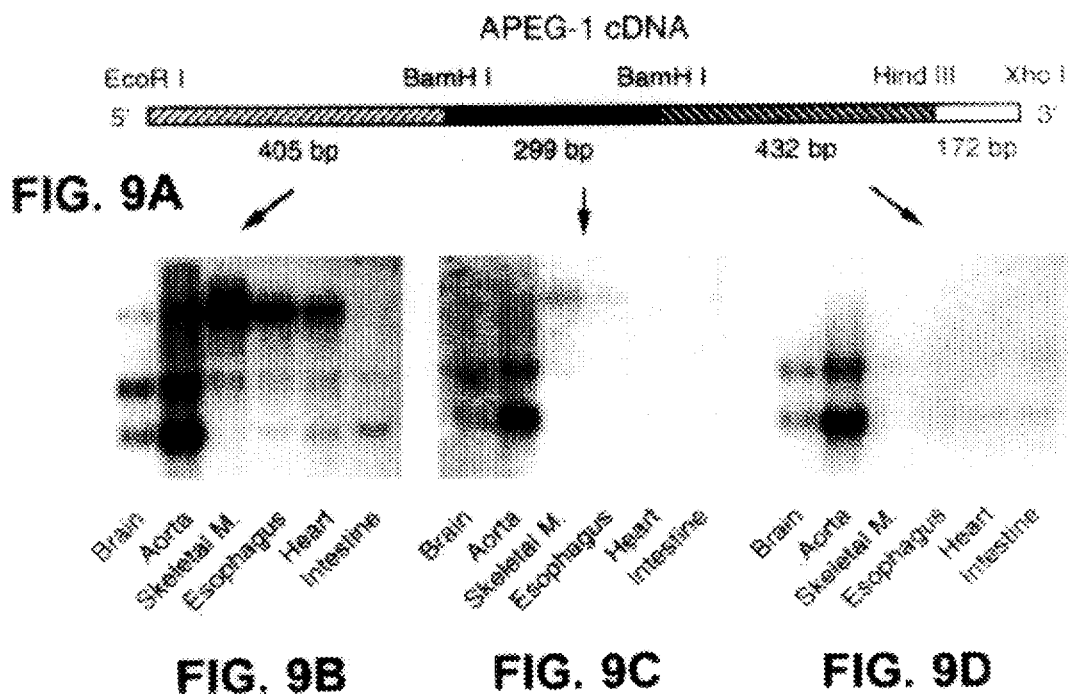
FIG. 9A
FIG. 9B  FIG. 9C  FIG. 9D
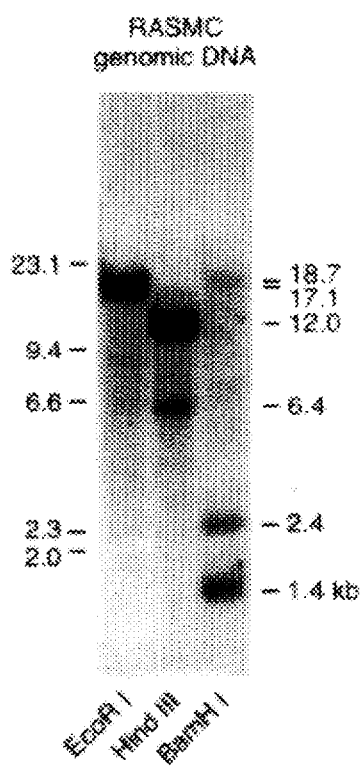
FIG. 10

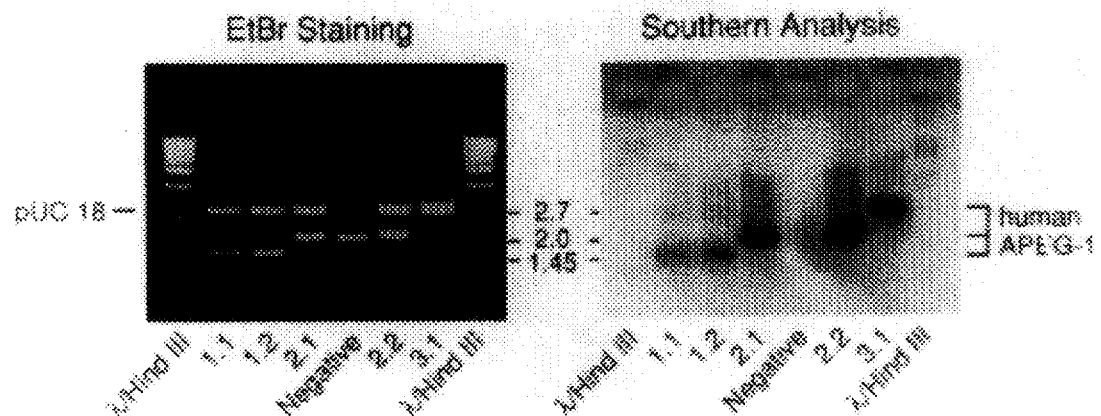
FIG. 11A  FIG. 11B
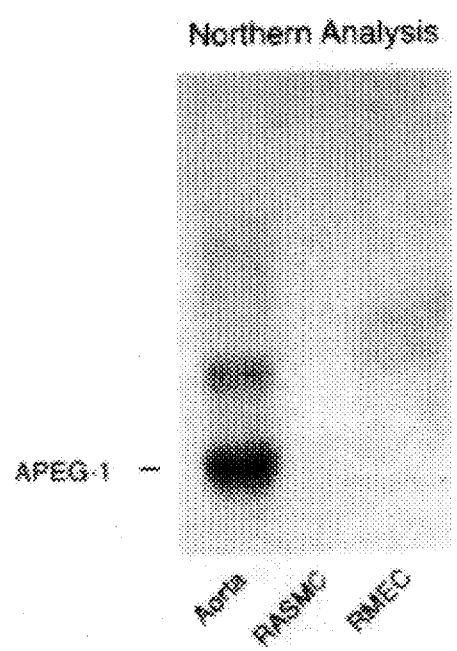
FIG. 12

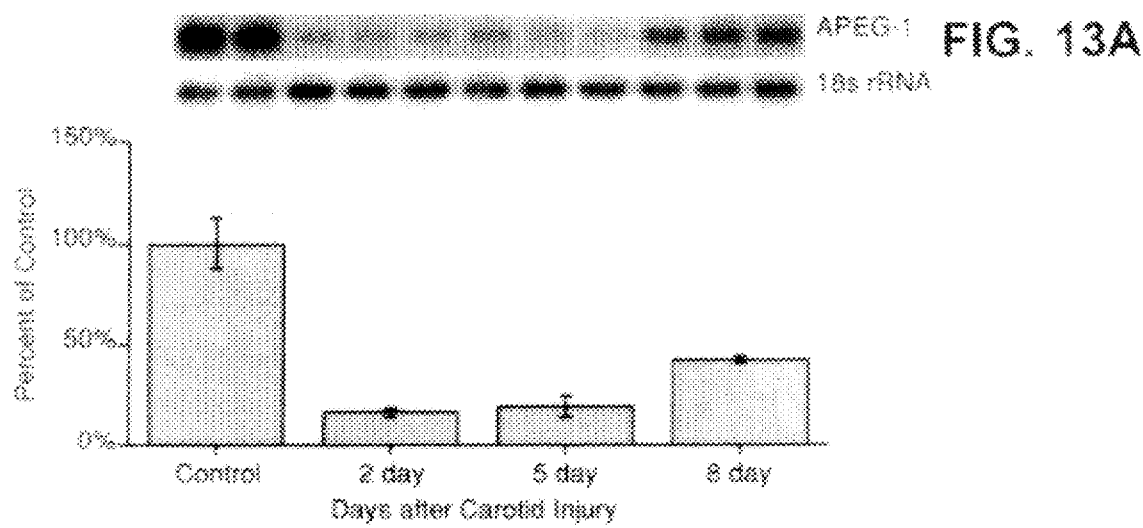
FIG. 13A
FIG. 13B
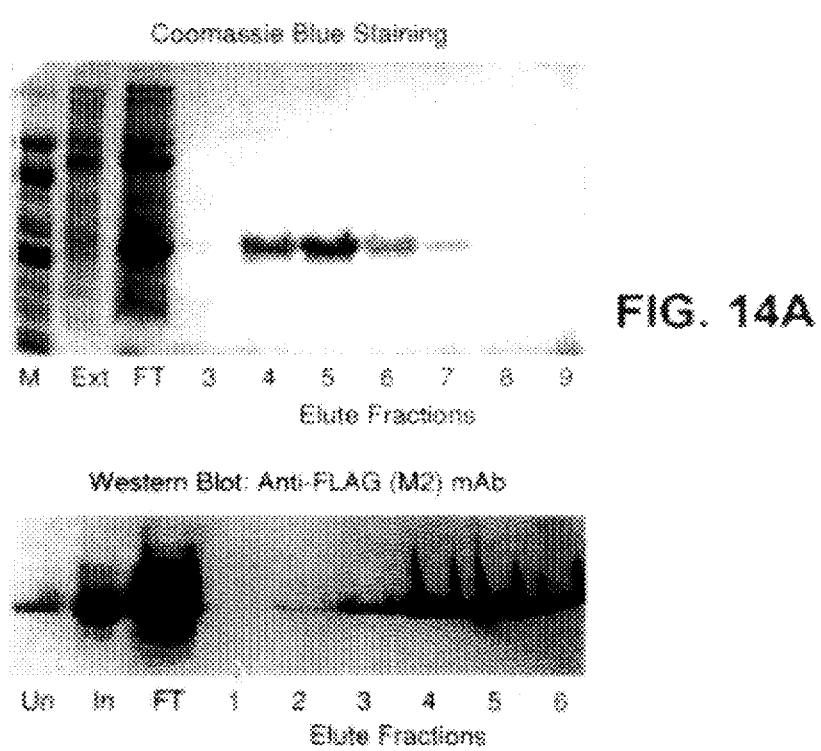
FIG. 14A
FIG. 14B

APEG-1 cDNA Sequence

```
   1  TCACCTCTGA TGAGGAATAC CTGAGCCCCC CAGAGGAGTT CCCAGAGCCT
  51  GGGGAGACCT GGCCGCGAAC CCCCACCATG AAGCCCAGTC CAGCCAGGA
 101  CCGCCGTTCT TCTGACACTG GCTCCAAGGC ACCCCCCACC TTCAAGGTCT
 151  CACTTATGGA CCAGTCAGTA AGAGAAGGCC AAGATGTCAT CATGAGCATC
 201  CGCGTGCAGG GGGAGCCCAA GCCTGTGGTC TCCTGGCTGA GAAACCGCCA
 251  GCCCGTGCGC CCAGACCAGC GGCGCTTTGC GGAGGAGGCT GAGGGTGGGC
 301  TGTGCCGGCT GCGGATCCTG GCTGCAGAGC GTGGCGATGC TGGTTTCTAC
 351  ACTTGCAAAG CGGTCAATGA GTATGGTGCT CGGCAGTGCG AGGCCCGCTT
 401  GGAGGTCCGA GGCGAGTGAG CTCAGGGGGC CACCTGCGCT CCCCCCGCTA
 451  CCCTCCGAGC CGCGCCCCTG TCTCAGGCAC CTCTCGGACC TCGCTGTGTT
 501  TCACTGCCTC CTGCCCACAG ACCCAGGCCT GCCGGCCCGG ACCCGTCCCA
 551  GCCTCCCCTC CCCACCCCAT GCAGCCCCCA GGGGATAGC  CCATGGGCCC
 601  CTGTGGACAC TCCCTCCCCA AGTGGACACA TGGCTGTGCA GGCCAGGAGG
 651  CCCACAGATG GACTGAGTGC TGGGAAGGGG CGGCTTCGAG GGGTATCAAC
 701  CCCCCGAGTC TCTCCCTGAA GGGGAGCACC GGGCGAGTGC ATGTGCTACT
 751  GCTGCTACAG GCCTGTCTAT CTGTTTGTCT GTCTGTGTGT CTGTGACAGT
 801  CAGGGAAGGA TGCCTCGGAG CTGAGGTGGG GTGAGACAGA GTGGGAGAGA
 851  TTACGGCATG GCATGGAGGG GCCCAAGGAG CAGGGGCTGT TGACAAAGGC
 901  CTTACCAGGA AGGGTTAGGA CACTGACCAT TCTAGAAATG GGTTTCGAAT
 951  GGCACAACAC TTTCTATTTC ACAAAAGACC AAAAGCCAGA GGCCCCAGGC
1001  TCTGTGCTGA TGAACAGCCT GGCTGAGCCC TGGCCCTGGC AGGTTTAGGG
1051  CCCATTTGGG GCCCCTCCT  TCTCTGTCAG GGCTGGGGTG CTCTGTCTGG
1101  GAATGAGGGA GTTAACCAAG TTTGGTGCAG GAGCAGGGC  AGGGGGCCAC
1151  TGTAGTGAGC GTGGATGAAA TTTGGANACA CCTATNTCTT AANTCAAATA
1201  AAGTCCAGTT TGTACCTAAA AAAAAAA    SEQ ID NO:11
```

FIG. 16

Predicted Human APEG-1 Peptide Sequence

```
  1  MKPSPSQDRR SSDTGSKAPP TFKVSLMDQS VREGQDVIMS IRVQGEPKPV
 51  VSWLRNRQPV RPDQRRFAEE AEGGLCRLRI LAAERGDAGF YTCKAVNEYG
101  ARQCEARLEV RGE*  SEQ ID NO:12
```

FIG. 17

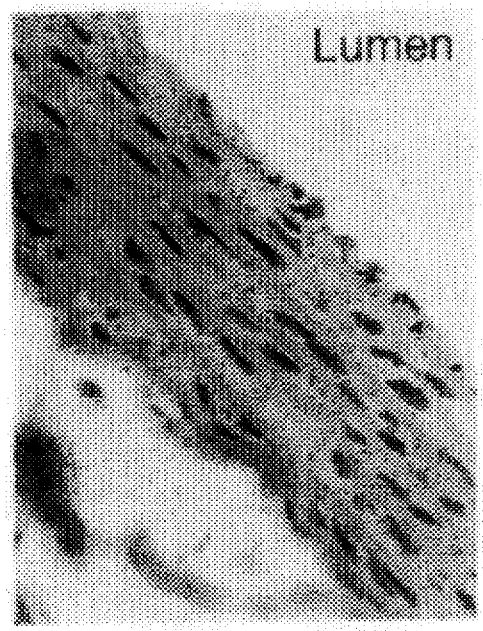 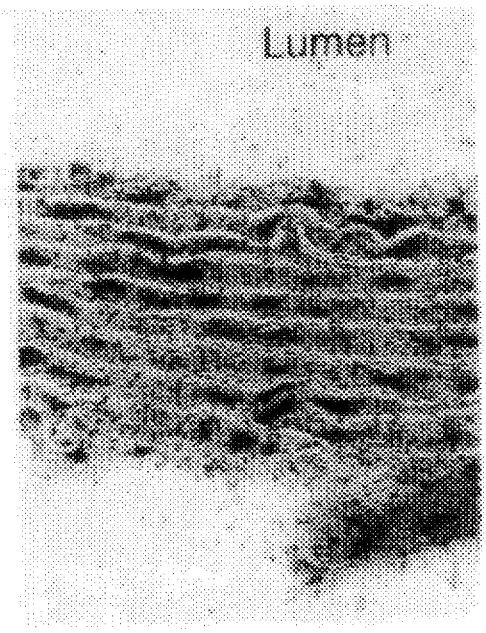
FIG. 18A  FIG. 18B

AORTIC PREFERENTIALLY EXPRESSED GENE AND USES THEREOF

BACKGROUND OF THE INVENTION

The invention relates to diagnosis and treatment of vascular injury.

Atherosclerosis and its subsequent complications, such as myocardial infarction, stroke, and peripheral vascular diseases, are the major causes of death in developed countries. Vascular endothelial and smooth muscle cells have important roles in the regulation of normal vascular tone. Damage or dysfunction of these cells can lead to vascular diseases, such as atherosclerosis and restenosis.

Atherosclerosis is believed to be a consequence of a response of the vascular wall to injury (Ross, R., 1993, Nature 362:801-9). Upon vascular injury and various other stimuli, cytokines and growth factors from activated vascular cells promote growth and migration of vascular smooth muscle cells in a dedifferentiated status, resulting in the formation of atherosclerotic plaques.

The pathogenesis of atherosclerosis is not fully understood, and an effective therapeutic regime has not been developed to prevent or cure atherosclerosis (Ross, R., The Pathogenesis of Atherosclerosis, in Heart Disease, a textbook of cardiovascular medicine, E. Braunwald, Editor, 1992, W. B. Saunders Company: Philadelphia. pp. 1106–24; and Ross, R.: The Pathogenesis of Atherosclerosis: a Perspective for the 1990s, 1993, Nature 362:801-9). Despite extensive research, the molecular mechanisms responsible for the regulation of gene expression in vascular endothelial and smooth muscle cells are largely unknown. In particular, trans-acting factors and cis-acting elements mediating vascular cell-specific gene expression have not been identified, mainly due to the fact that only a few vascular specific genes have been identified. Furthermore, of the genes that have been characterized as endothelial cell-specific (e.g. von Willebrand factors, VEGF receptor flk-1, VCAM-1, and E-selection (Hunter, J. J., et al., 1993, Hypertension 22:608-17) or smooth muscle cell-specific (e.g., CHIP28, SM22, and gax (Gorski, D. H., et al., 1993, Mol. Cell. Biol. 13(6):3722-33), many have been found in other cell types at various levels.

SUMMARY OF THE INVENTION

The invention is based on the discovery of a novel gene the expression of which is specific to aortic cells. Accordingly, the invention features an aortic cell-specific gene, and therefore provides a substantially pure DNA (e.g., genomic DNA, cDNA or synthetic DNA) encoding an aortic-preferentially-expressed gene-1 (APEG-1) polypeptide. By "substantially pure DNA" is meant DNA that is free of the genes which, in the naturally-occurring genome of the organism from which the DNA of the invention is derived, flank the APEG-1 gene. The term therefore includes, for example, a recombinant DNA which is incorporated into a vector, into an autonomously replicating plasmid or virus, or into the genomic DNA of a prokaryote or eukaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

The DNA may encode a naturally occurring mammalian APEG-1 polypeptide such as a rat APEG-1 polypeptide (SEQ ID NO:3) or human APEG-1 polypeptide (SEQ ID NO:12). For example, the invention includes degenerate variants of SEQ ID NO:2 or SEQ ID NO:11. The invention also includes a substantially pure DNA comprising a strand which hybridizes at high stringency to a DNA having the sequence of SEQ ID NO:1, 2, or 11, or the complements thereof.

Hybridization is carried out using standard techniques such as those described in Ausubel et al., Current Protocols in Molecular Biology, John Wiley & Sons, (1989). "High stringency" refers to DNA hybridization and wash conditions characterized by high temperature and low salt concentration, e.g., wash conditions of 65° C. at a salt concentration of approximately 0.1×SSC. "Low" to "moderate" stringency refers to DNA hybridization and wash conditions characterized by low temperature and high salt concentration, e.g. wash conditions of less than 60° C. at a salt concentration of at least 1.0×SSC. For example, high stringency conditions may include hybridization at about 42° C., and about 50% formamide; a first wash at about 65° C., about 2×SSC, and 1% SDS; followed by a second wash at about 65° C. and about 0.1%×SSC. Lower stringency conditions suitable for detecting DNA sequences having about 50% sequence identity to an APEG-1 gene are detected by, for example, hybridization at about 42° C. in the absence of formamide; a first wash at about 42° C., about 6×SSC, and about 1% SDS; and a second wash at about 50° C., about 6×SSC, and about 1% SDS.

A substantially pure DNA having at least 50% sequence identity (preferably at least 70%, more preferably at least 80%, and most preferably at least 90%) to SEQ ID NO:1, 2, or 11, and encoding a polypeptide having a biological activity of an APEG-1 polypeptide is also within the invention. The percent sequence identity of one DNA to another is determined by standard means, e.g., by the Sequence Analysis Software Package developed by the Genetics Computer Group (University of Wisconsin Biotechnology Center, Madison, Wis.) (or an equivalent program), employing the default parameters thereof. "Biological activity of an APEG-1 polypeptide" is defined as the ability to inhibit the proliferation or migration of smooth muscle cells at the site of vascular injury.

The invention also includes a substantially pure DNA containing a constitutive or inducible, vascular cell-specific promoter, e.g., an APEG-1 promoter which is preferably in a vector into which an heterologous gene may be or has been cloned, and under the control of which the gene may be expressed. The promoter is preferably specific for arterial cells (e.g., cells of the aorta), and most preferably specific for vascular smooth muscle cells. DNA encoding APEG-1 may be operably linked to such regulatory sequences for expression of the APEG-1 polypeptide in vascular cells.

By "promoter" is meant a minimal DNA sequence sufficient to direct transcription. Promoters may be constitutive or inducible, and may be coupled to other regulatory sequences or "elements" which render promoter-dependent gene expression cell-type specific, tissue-specific or inducible by external signals or agents; such elements may be located in the 5' or 3' region of the native gene, or within an intron.

By "operably linked" is meant that a coding sequence and a regulatory sequence(s) are connected in such a way as to permit gene expression when the appropriate molecules (e.g., transcriptional activator proteins) are bound to the regulatory sequence(s).

The invention also provides a method of directing vascular cell-specific expression of a protein by introducing into a vascular cell an isolated DNA containing a sequence encoding the protein operably linked to the vascular cell-specific promoter. A cell containing the DNA or vector of the invention is also within the invention.

The invention also features a substantially pure APEG-1 polypeptide (e.g., rat APEG-1 (SEQ ID NO:3) or human APEG-1 (e.g., human APEG-1 (SEQ ID NO:12)) and an antibody which specifically binds to an APEG-1 polypeptide. By a "substantially pure polypeptide" is meant a polypeptide which is separated from those components (proteins and other naturally-occurring organic molecules) which naturally accompany it. Typically, the polypeptide is substantially pure when it constitutes at least 60%, by weight, of the protein in the preparation. Preferably, the protein in the preparation is at least 75%, more preferably at least 90%, and most preferably at least 99%, by weight, APEG-1 polypeptide. A substantially pure APEG-1 polypeptide may be obtained, for example, by extraction from a natural source (e.g., an aortic cell); by expression of a recombinant nucleic acid encoding an APEG-1 polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include recombinant polypeptides derived from a eukaryote but produced in *E. coli* or another prokaryote, or in a eukaryote other than that from which the polypeptide was originally derived.

In another aspect, the invention provides a method of detecting injury in a sample of vascular tissue by determining the level of APEG-1 gene expression in the tissue; a decrease in the level of expression detected in the tissue sample compared to that detected in uninjured control vascular tissue indicates the presence of a vascular injury.

The invention also includes a method of inhibiting smooth muscle cell proliferation in an animal by contacting an artery of the animal with an APEG-1 polypeptide or a biologically active fragment thereof or with a compound that stimulates the APEG-1 promoter, e.g., stimulates APEG-1 expression.

In yet another aspect, the invention includes a method of making an APEG-1 polypeptide, e.g., a rat or human APEG-1 polypeptide, involving providing a cell containing DNA encoding an APEG-1 polypeptide and culturing the cell under conditions permitting expression of the APEG-1-encoding DNA, i.e., production of the recombinant APEG-1 by the cell.

Other features and advantages of the invention will be apparent from the following description of the preferred embodiments thereof, and from the claims.

DETAILED DESCRIPTION

The drawings will first be described.

FIG. 1 is a flow chart of the differential mRNA display procedure for identifying APEG sequences.

FIG. 2A is a photograph of a differential mRNA display showing APEG-1 preferentially expressed in the rat aorta. The differential expression was tested among 6 rat tissues. Unique bands in the aorta that were eluted and reamplified for subsequent analysis are indicated (▮

FIG. 2B is a photograph of a differential mRNA display showing APEG-2 preferentially expressed in the rat aorta. The differential expression was tested among 6 rat tissues. Unique bands in the aorta that were eluted and reamplified for subsequent analysis are indicated (▮

FIG. 2C is a photograph of a differential mRNA display showing APEG-3 preferentially expressed in the rat aorta. The differential expression was tested among 6 rat tissues. Unique bands in the aorta that were eluted and reamplified for subsequent analysis are indicated (▮

FIG. 2D is photograph of a differential mRNA display showing APEG-4 preferentially expressed in the rat aorta. The differential expression was tested among 6 rat tissues. Unique bands in the aorta that were eluted and reamplified for subsequent analysis are indicated (▮

FIG. 2E is a photograph of a Northern blot analysis showing tissue expression of APEG-1. Ten micrograms of total RNA from each tissue were used in Northern analysis. The loading of each tissue RNA was normalized by comparing 18s rRNA hybridization signals (shown in FIG. 2F).

FIG. 2F is a photograph of a Northern blot analysis showing 18s rRNA.

FIG. 2G is a photograph of a Northern blot analysis showing tissue expression of APEG-2. Ten micrograms of total RNAs from each tissue were used in Northern analysis, and the loading of each tissue RNA was normalized by comparing 18s rRNA hybridization signals.

FIG. 2H is a photograph of a Northern blot analysis showing tissue expression of APEG-3. Ten micrograms of total RNAs from each tissue were used in Northern analysis, and the loading of each tissue RNA was normalized by comparing 18s rRNA hybridization signals.

FIG. 2I is a photograph of a Northern blot analysis showing tissue expression of APEG-4. Ten micrograms of total RNAs from each tissue were used in Northern analysis, and the loading of each tissue RNA was normalized by comparing 18s rRNA hybridization signals.

Figure 1:
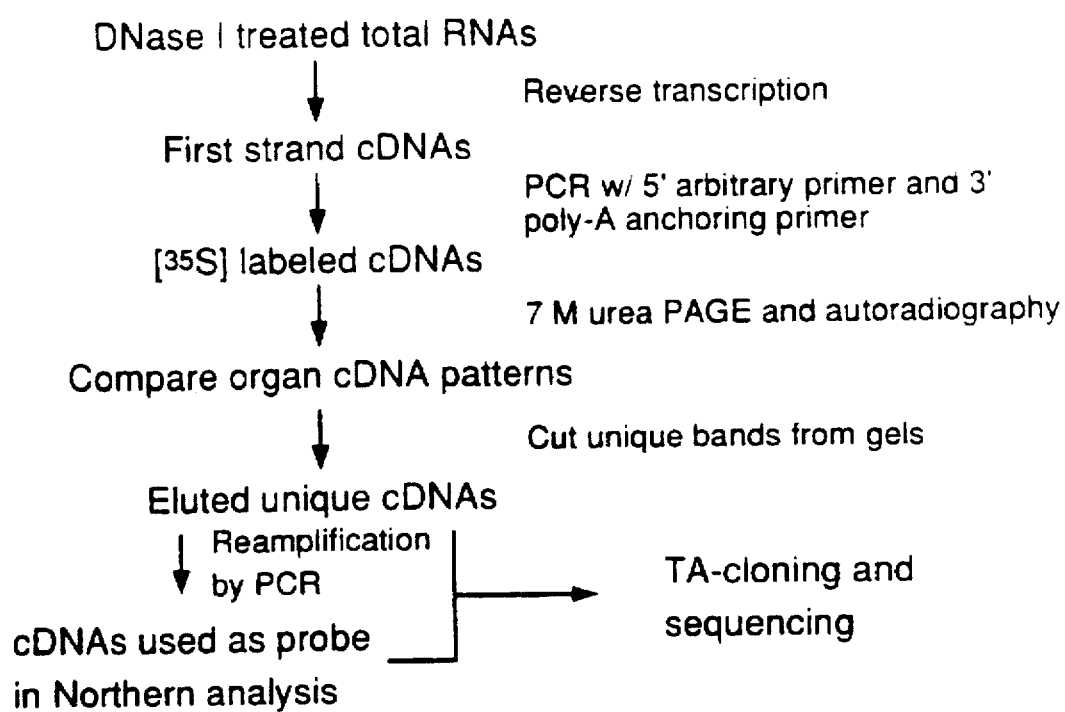

FIG. 3A is a photograph of a Northern blot analysis using full length CDNA of APEG-1 (APEG-1 full cDNA) as a probe. Samples of RNA from twelve rat organs were analyzed. The respective lanes are labelled in FIG. 3D.

FIG. 3B is a photograph of a Northern blot analysis using a 3' cDNA fragment originally cloned by differential mRNA display (APEG-1 3' D.D. frag.) as a probe. Samples of RNA from twelve rat organs were analyzed.

FIG. 3C is a photograph of a Northern blot showing 18s rRNA bands (18s rRNA) to which RNA loading was normalized.

FIG. 3D is a bar graph showing tissue distribution of APEG-1 gene expression.

FIG. 4 is a flow chart showing the cloning strategy for APEG-1. A rat aortic cDNA library established in the yeast expression vector pcJATA was screened to isolate full length APEG-1 cDNA. Southern analysis was carried out to confirm the presence of APEG-1 in this cDNA library. Restriction enzyme-digested (EcoRI and XhoI) cDNA fragments were separated on an agarose gel and the portions that contained APEG-1 cDNA, as determined by size markers and Southern analysis, were excised to elute the cDNA contents. Eluted cDNAs were ligated with linearized pSP72 vectors, and the ligated DNAs were used to transform competent *E. coli* DHα5 cells to establish a size-selected aortic cDNA sublibrary. This CDNA sublibrary was screened by the APEG-1 CDNA 3' fragment to obtain its full length CDNA.

FIG. 5 is a diagram of the nucleotide sequence of rat APEG-1 CDNA (SEQ ID NO:1). The longest open reading frame is located from nucleotide 169 to 511 (BOLD UPPERCASE) and the ATG flanking nucleotides that match the Kozak consensus sequence are indicated (UPPERCASE). A very short upstream open reading frame is present from nucleotide 102 to 116 (italic). There is a polyadenylation signal (underline) 21 nucleotides upstream of the poly-A tail. The primer annealing site of the 5' arbitrary primer used in the initial differential display PCR is also indicated (ITALIC UPPERCASE).

FIG. 6 is a diagram of the amino acid sequence (SEQ ID NO:3) deduced from the longest APEG-1 cDNA open reading frame (SEQ ID NO:2). Possible phosphorylation sites of protein kinase C and casein kinase-2 are indicated (bold). An integrin binding site, RGD, is also shown (bold italic). "***" represents a stop codon.

FIG. 7A is a photograph of in vitro transcription products of the APEG-1 gene. The 1.3 kb APEG-1 cDNA and a positive control DNA template were transcribed by T7 RNA polymerase. 1 µl of the 20 µl RNA products were resolved on a 1.2% denaturing agarose gel.

FIG. 7B is a photograph of in vitro translation products of the APEG-1 gene. In vitro transcribed APEG-1 mRNA was translated by wheat germ extract in the presence of [$^{35}$S]-methionine, and separated on a 10% tricine-SDS-polyacrylamide gel. In the mock reaction, mRNA template was absent.

FIG. 8 is an alignment of amino acid sequences of APEG-1 (SEQ ID NO:8), the myosin light chain kinase of chicken (ChkMLCK; SEQ ID NO:5) and of rabbit (RabMLCK; SEQ ID NO:7), and telokin of chicken (ChkTelo; SEQ ID NO:4) and of rabbit (RabTelo; SEQ ID NO:6). A consensus sequence (SEQ ID NO:9) is also shown to indicate the amino acid residues that are identical among these proteins. The conserved serine residue that is phosphorylated by cAMP-dependent protein kinase is marked by an asterisk (*).

FIG. 9A is a diagram of APEG-1 CDNA. APEG-1 cDNA was divided into four fragments by EcoR I, BamHI, Hind III, and XhoI restriction enzyme digestion. The three large fragments (405, 299, and 432 bp) were used to probe six rat tissue RNAs to show their different hybridization patterns.

FIG. 9B is a photograph of a Northern analysis using the 405 bp fragment of APEG-1 cDNA as a probe.

FIG. 9C is a photograph of a Northern analysis using the 299 bp fragment of APEG-1 cDNA as a probe.

FIG. 9D is a photograph of a Northern analysis using the 432 bp fragment of APEG-1 cDNA as a probe.

FIG. 10 is a photograph of a genomic Southern analysis of the APEG-1 gene. Genomic DNA from cultured rat aortic smooth muscle cells was harvested and digested with EcoRI, HindIII, or BamHI. APEG-1 full length cDNA was used as probe in the Southern analysis. The size of each band (indicated on the right) was determined according to the size markers (indicated on the left).

FIG. 11A is a photograph of ethidium bromide staining of the 3 clones of human homologues of rat APEG-1. Clone 1 (1.1, 1.2), clone 2 (2.1, 2.2), and clone 3 (3.1) were 1.45, 2.0, and 2.7 kb in size, respectively.

FIG. 11B is a photograph of a Southern analysis showing hybridization of these human homologues with a rat APEG-1 cDNA probe.

FIG. 12 is a photograph of a Northern analysis of APEG-1 expression in vitro. RNAs from rat aortic smooth muscle cells (RASMC) and from microvascular endothelial cells (RMEC) were purified and separated on a 1.2% denaturing agarose gel. RNA from normal rat aorta was used as a positive control. APEG-1 CDNA was used as probe in Northern analysis to examine its expression in these two cell types.

FIG. 13A is a photograph of a Northern analysis showing expression of APEG-1 in rat carotid artery during balloon injury. RNAs were purified from rat carotid arteries 2, 5, 8 days after balloon injury. Three injured rats were used in each time point and two uninjured rats were used as control. The APEG-1 cDNA was used in Northern analysis and the band intensities were normalized by 18s rRNA signal.

FIG. 13B is a bar graph showing expression of APEG-1 in rat carotid artery during balloon injury. Each column represents the mean expression of APEG-1 in the Northern analysis bands shown in FIG. 13A, expressed as a percent of control ± one standard error.

FIG. 14A is a photograph of a Coomassie blue stained 10% tricine-SDS-PAGE gel showing the purified FLAG-APEG-1 fusion protein. M, protein size marker. Ext, induced bacterial cell extracts. FT, cell extract that flowed through the FLAG peptide affinity column.

FIG. 14B is a photograph of a Western analysis of the purified fusion protein. A monoclonal anti-FLAG peptide antibody, M2 (IBI), was used to identify the purity of the fusion protein. Un, uninduced bacterial cell extracts. In, induced bacterial cell extracts. FT, cell extract that flowed through the FLAG peptide affinity column.

Figure 15:
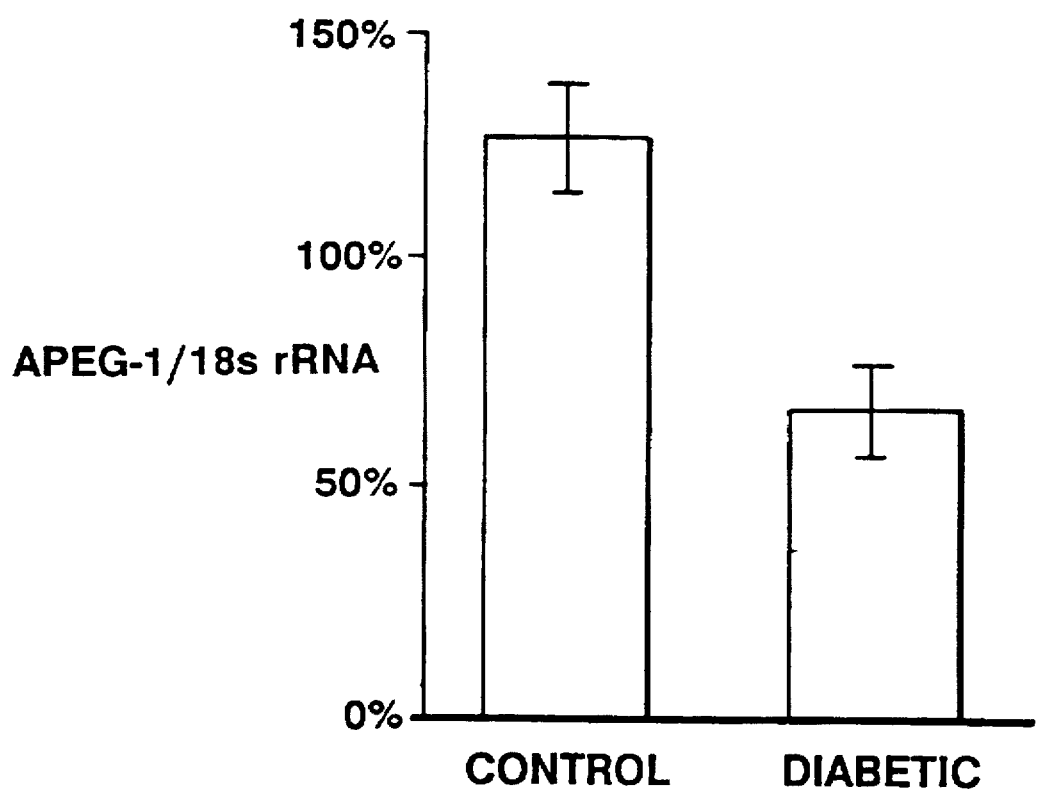

FIG. 15 is a bar graph comparing APEG-1 expression in diabetic rats and control rats. APEG-1 expression was decreased in diabetic rats (unpaired T test: $T_{10}=3.284$, p value=0.0033).

FIG. 16 is a diagram showing the CDNA sequence of human APEG-1 (SEQ ID NO:11)

FIG. 17 is a diagram showing the amino acid sequence of human APEG-1 (SEQ ID NO:12). "*" represents a stop codon.

FIG. 18A is a photograph showing the results of an in situ hybridization experiment. The lumen of a rat aorta was sectioned and hybridization carried out using a rat APEG-1 sense strand DNA probe as a control.

FIG. 18B is a photograph showing APEG-1 mRNA expression in the lumen of a rat aorta. In situ hybridization was carried out using a rat antisense strand DNA probe to measure rat APEG-1 expression in aortic tissue.

Purification of total RNAs

Total RNA was harvested from male Sprague-Dawley rat organs. The dissected organs were washed in phosphate buffered saline and snap-frozen in liquid nitrogen. The adventitia of the aorta was stripped, and the contents of the small intestine were removed before freezing. The frozen organs were homogenized and RNAs were harvested by acid guanidinium thiocyanate-phenol-chloroform extraction (Chomczynski, P. et al., 1987, Anal. Biochem. 162(1):156–9). The cell culture RNAs were purified by guanidinium/CsCl ultracentrifugation.

Differential mRNA Display

Fifty micrograms of total RNA were treated with DNase I (Boehringer Mannheim) to remove contaminating genomic DNA in the presence of RNase inhibitor RNasin (Promega). After phenol/chloroform extraction and ethanol precipitation, the RNA concentration was adjusted to 0.1 µg/ml in DEPC-treated dH20. First strand cDNA was synthesized using MMLV reverse transcriptase (GIBCO, BRL) with the 3' poly-A-anchoring primer $T_{12}VG$ (5'-

TTTTTTTTTTTTVG-3') (SEQ ID NO:10). Subsequently the reaction was heated at 95° C. to inactivate reverse transcriptase, and the cDNA products were stored at −20° C. Two microliters of the CDNA were used in 20 μl PCR reactions (2 μl cDNA, 0.2 μM 5' arbitrary primer, 1 μM 3' $T_{12}$VG primer, 1.5 mM $Mg^{2+}$, 2.5 μM dNTP, 12.5 μCi $^{35}$S-dATP, 1 unit Taq DNA polymerase; 94° C. for 15 sec, the thermal cycling was 40° C. for 30 sec and 72° C. for 30 sec; the thermal cycling was repeated for 40 cycles) following the reverse transcription. Sample loading buffer (98% formamide, 0.05% bromophenol blue, and 0.05% xylene cyanol) was added, and the samples were heated at 95° C. before loading onto a 6% sequencing gel. Overnight exposure of the dried sequencing gels to X-OMAT films (Kodak) was usually sufficient to display the differential mRNA patterns.

Reamplification of eluted cDNAs

Bands of interest on the dried gel were excised, soaked in 200 μl $dH_2O$ for 10 minutes at room temperature, and eluted by heating at 95° C. for 15 minutes. After a brief centrifugation, the supernatants were transferred into fresh tubes, and the eluted DNAs were ethanol-precipitated at −20° C. in the presence of 20 μg glycogen and 300 mM sodium acetate. The precipitated DNAs centrifugation and centrifugation and washed with 70% ethanol. Dried DNA pellets were resuspended in 10 μl $dH_2O$ and nonradioactively reamplified by PCR with the same initial PCR primers and condition, except that the reaction volume was scaled up to 100 μl with 25 μM dNTP. Reamplified cDNAs were resolved on 1% agarose gel to determine their sizes and amounts.

RNA gel electrophoresis and Northern blotting

Ten micrograms of total RNA were heat-denatured and loaded on a denaturing agarose gel (1.2% agarose, 1.1% formaldehyde, 0.5 μg/ml ethidium bromide in MOPS buffer). Electrophoresis was carried out at 10 V/cm for three to four hours. A photograph of the ethidium bromide staining pattern of the RNAs was taken under UV light illumination. The RNAs were then transferred onto a Nitropure membrane (Micron Separation Inc.) by standard blotting procedure (Ausubel, F. M., et al., ed. Current Protocols in Molecular Biology. ed. K. Janssen., 1994, Vol. 1., Current Protocols:4.9.1–14).

DNA gel electrophoresis and Southern blotting

DNAs were loaded and separated on a 1% agarose gel, followed by standard Southern blotting (Ausubel, F. M., et al., ed. Current Protocols in Molecular Biology. ed. K. Janssen., 1994, Vol. 1, Current Protocols: 2.9.1–15). The DNAs in the gel were denatured in denaturation buffer (1.5M NaCl, 0.5N NaOH), then neutralized in neutralization buffer (1.5M NaCl, 1M TrisCl, pH 7.4) prior to being transferred onto a Nitropure membrane in 20×SSC solution overnight.

Random priming and hybridization

Radioactive DNA probes were generated by random priming (Boehringer Mannheim) with 25 to 50 ng of the DNA fragment. Hybridization to the DNA or RNA blots was carried out in QuikHyb solution (Stratagene) with $1 \times 10^6$ cpm/ml of radioactive probes and 0.2 mg/ml herring sperm DNA (Boehringer Mannheim) at 68° C. for one to two hours. The blots were washed and exposed to X-ray films for permanent records.

Quantitation of hybridization signals

To quantitate the hybridization signals, DNA and RNA blots were exposed to phosphor screens (Molecular Dynamics) overnight. The phosphor screens were then scanned by a PhosphoImager scanner (Molecular Dynamics) operated by the ImageQuant program (Molecular Dynamics) running on a PC-DOS/MS Windows computer system (Compaq). Intensities of the signals were quantified by the same ImageQuant program following the manufacturer's instructions.

DNA sequencing and sequence analysis

Dideoxynucleotide chain termination DNA sequencing method was used to sequence DNAs. One microliter of DMSO was always included to reduce the DNA template secondary structures that may interfere with the Sequenase (USB) enzymatic activity. The sequences were resolved on 8% sequencing gel (National Diagnostics). The DNA sequences were stored into a local computer mainframe (mbcrr.harvard.edu), and analyzed by a sequence analysis software package (Genetics Computer Group).

Fusion protein expression and purification

Rat APEG-1 cDNA was cloned into pFLAG-2 vector, then transformed into *E. coli* BL21 cells. Transformed BL21 cells were grown in large scale to an optical density ($OD_{595}$) of 1.75. The cell pellet was resuspended in extraction buffer (20 mM TrisCl, pH 7.4, 0.2 mM EDTA, 1M NaCl, 1 mM PMSF, 1 mM DTT) and sonicated on ice, after which the extract was frozen and thawed three times in liquid nitrogen and a 42° C. water bath. The soluble cell extract was collected by centrifugation (12,000×g, 4° C., 20 minutes) and used in purification of the fusion protein by affinity chromatography with a M2 anti-FLAG peptide mAb affinity column. The column, loaded twice with the soluble cell extract, was washed sequentially with 50 ml of each of the following solutions, TE/NaCl/NP-40 buffer (20 mM TrisCl pH 7.4, 0.2 mM EDTA, 150 mM NaCl, 0.5% NP-40), TE/NaCl buffer (20 mM TrisCl pH 7.4, 0.2 mM EDTA, 150 mM NaCl), and TE buffer (20 mM TrisCl pH 7.4, 0.2 mM EDTA). The FLAG-APEG-1 fusion protein was eluted with 10 ml glycine buffer (0.1M glycine, pH 3.0) and the eluates were slowly collected in 0.8 ml fractions into microfuge tubes containing 50 μl 1M TrisCl, pH 8.0, and 150 μl 5M NaCl solutions. The purity of the purified fusion proteins was assayed by protein electrophoresis and Coomassie blue staining as well as western blotting with anti-FLAG mAb.

Protein gel electrophoresis and western blotting

A 10% tricine-SDS-polyacrylamide gel system was used to separate bacterial-expressed pFLAG-APEG-1 fusion protein (Schägger, H. et al., 1987, Anal. Biochem. 166:368–79). This system was used because a 10% tricine-SDS-polyacrylamide gel has superior resolution for proteins less than approximately 14 kDa compared to a standard glycine-SDS-polyacrylamide gel. After electrophoresis, the protein gel was assembled in a semi-dry transfer apparatus (Hoefer) and the protein samples were transferred onto a PVDF membrane (Millipore) in transferring buffer (25 mM Tris base, 200 mM glycine, 20% methanol) at 125 mA for one hour.

In vitro transcription and translation

Rat APEG-1 cDNA was cloned into the pSP72 vector and linearized so that RNA could be transcribed from its upstream T7 promoter with the T7 RNA polymerase. Transcription was carried out in a large-scale T7 transcription system (Novagen) in the presence of 7-$^{me}$GpppGTP to produce capped mRNA. The in vitro transcribed mRNA was translated in an in vitro translation system of wheat germ extract (Promega) with the [$^{35}$S]-methionine to produce radiolabeled proteins.

Cell culture

Primary rat aortic smooth muscle cells were maintained in DMEM medium supplied with 10% fetal calf serum, 4 mM L-glutamine, 10 mM HEPES, 100 U/ml penicillin and 100 ng/ml streptomycin. Primary rat microvascular endothelial cells were maintained in DMEM medium supplied with 20% fetal calf serum, 4 mM L-glutamine, 100 U/ml penicillin and 100 ng/ml streptomycin.

Plasmid DNA purification

The mini- (<20 μg) and midiscale (<200 μg) preparations of plasmid DNA were purified by DNA-affinity chromatography (Qiagen). Large scale purification of plasmid DNA was carried out according to the alkaline lysis/CsCl ultracentrifugation methods (Ausubel, F. M., et al., ed. Current Protocols in Molecular Biology. ed. K. Janssen., 1994, Vol. 1, Current Protocols: 1.7.1–11).

Purification of recombinant λgt11 DNA

Single positive plaques were picked and soaked in the suspension medium (0.1M NaCl, 10 mM $MgSO_4$, 50 mM TrisCl, pH 7.5, and 0.01% gelatin) with one drop of $CHCl_3$. Freshly prepared *E. coli* strain Y1090 competent cells were mixed and incubated briefly with the resuspended phage. The infected cells were grown overnight in LB medium with 10 mM $MgSO_4$ and 0.2% maltose. The next morning one drop of chloroform was added into the medium to lyse the bacterial cells for 15 minutes. Bacterial debris was collected by centrifugation, and to the clear supernatant 100 U DNase I and 100 ng RNase A were added to digest *E. coli* genomic DNA and RNA. The solutions of EDTA, TrisCl (pH 8.0), NaCl, and proteinase K were added subsequently to final concentrations of 50 mM, 100 mM, 200 mM, and 100 ng/ml, respectively. The mixture was incubated at 42° C. for 30 minutes. Phage DNA was then phenol/chloroform extracted once and precipitated by adding 0.6×volume of isopropanol in the presence of 300 mM NaOAc. Precipitated phage DNA was recovered by centrifugation and washed with 70% ethanol, air dried, then dissolved in 250 μl TE buffer (10 mM TrisCl, pH 8.0, 1 mM EDTA).

Cloning APEG-1 genes

To clone genes that are preferentially expressed in the aorta, total organ RNA was prepared from rat aorta with the adventitia removed, and from brain, skeletal muscle, esophagus, heart, and intestine. Using the differential mRNA display technique, a technique that systematically amplifies mRNAs by means of RT-PCR with different sets of 5' arbitrary primers and 3' oligo-dT anchoring primers, the mRNA patterns of different organs were compared. The PCR products were resolved on a denaturing polyacrylamide sequencing gel to display mRNA patterns that distinguish one organ from another. The bands that were separated by gel electrophoresis represent the 3'-termini of the cDNAs. Therefore, a band that is present in one organ but not in the others suggests that the gene is only expressed in that particular organ (FIG. 1). Specific mRNAs that were present solely in the aorta were identified and cloned.

The organ RNAs were screened with thirty-three 5' arbitrary primers in combination with a $T_{12}VG$ 3' oligo-dT anchoring primer. This initial screening covered 21 percent of the 160 primer combinations needed to screen all possible mRNAs to be displayed by this technique. This estimate is based on the assumption that one primer combination displays about 100 different mRNAs from approximately 15,000 different mRNA species present in each cell.

From the initial screening, seventeen bands that were present solely in the aorta were identified. These bands were cut from the gel and the cDNA fragments eluted and reamplified by PCR with the same primers that were used in their original RT-PCRs. These reamplified cDNAs were $^{32}$P-labeled, then used in Northern blot analyses to confirm their aortic specificity. Four cDNA fragments were found to be aorta-specific (FIGS. 2A–2I). After cloning these four cDNA fragments by TA-cloning methods, the clones were designated APEG-1, APEG-2, APEG-3, and APEG-4. Their DNA sequences were determined by the dideoxynucleotide chain termination method and compared to known DNA sequences listed in the GENBANK® database. APEG-2 showed identical sequences to the rat SM22 gene (Shanahan, C. M., et al., 1993, Circ. Res. 73(1):193–204), a smooth muscle cell specific gene. APEG-4 was found to have a near-identical sequence to chicken and mouse TIMP-3 genes (tissue inhibitor of metalloproteinase-3) (Sun, Y., et al., 1994, Cancer Res. 54:1139–44; Leco, K. J., et al., 1994, J. Biol. Chem. 269(12):9352–60). APEG-1 and APEG-3 did not match any known genes. Further examination of the tissue distribution of expression showed that APEG-3 was also expressed in the lung, a result not seen in the initial Northern blot analysis. In contrast, APEG-1 showed the highest expression in the aorta among twelve rat organs (FIGS. 3A–3D), thus confirming the specificity of tissue expression.

Cloning and sequence analysis of rat APEG-1 CDNA

The APEG-1 3' CDNA fragment, derived from differential RNA display, was used to screen a rat aortic cDNA library (FIG. 4). The cloned APEG-1 cDNA was determined to be 1,308 base pairs, consistent with the size of the message seen in Northern blot analysis. Sequences of both cDNA strands were determined by dideoxynucleotide chain termination sequencing with fragment-subcloning and oligonucleotide-walking strategies. The complete cDNA sequence had no homologous counterpart in the GENBANK® database.

The rat APEG-1 cDNA can then be used to screen a genomic library to obtain the vascular cell-specific promoter sequences which regulate expression cell-specific expression of APEG-1.

To analyze the protein encoded in APEG-1 cDNA, the sequence was searched for possible ATG initiation codons for translation from the 5' end of the sequence. The longest open reading frame in the rat APEG-1 cDNA (SEQ ID NO:1) spans from 169 to 511 nucleotides (SEQ ID NO:2) downstream of the 5' end of the cDNA. Another ATG sequence was found at nucleotide 102 to 104 (FIG. 5), but the possible translation from this preceding ATG codon is terminated after four amino acid residues, thus making it unlikely to be the initiation codon used in vivo. The longest open reading frame has a Kozak consensus sequence (Kozak, M., 1987, J. Mol. Biol. 196:947–50) and encodes a protein of 113 amino acids (SEQ ID NO:3) with a predicted molecular weight of 12.667 daltons and an estimated pI of 9.125 (FIG. 6). This predicted translation product was confirmed by in vitro transcription and in vitro translation of the APEG-1 cDNA, which yielded a major translation product of 12.7 kDa as predicted by the deduced amino acid sequence from the longest open reading frame (FIGS. 7A–7B). Comparison of the APEG-1 deduced amino acid sequence to the SwissProt protein database again showed no identical protein sequence. However, a region was identified that is homologous to proteins of the myosin light chain kinase family, which includes myosin light chain kinases and telokin (FIG. 8).

The myosin light chain kinases (MLCKs), present in all eukaryotic cells, are members of the $Ca^{2+}$-calmodulin-dependent protein kinases. They phosphorylate the 20 kDa light chain subunit of myosin, a protein that is important in regulating contraction of smooth muscle cells, secretory vesicle movement, cellular locomotion, and changes in cellular morphology (Gallagher, P. J., et al., 1991, J. Biol. Chem. 266(35):23945–52). The structure of MLCKs is highly conserved and composed of several modular domains. The MLCK carboxyl terminus is the calmodulin-binding domain and has a regulatory function mediated by two specific serines residues which become phosphorylated by cAMP-dependent protein kinase. Phosphorylation at these two sites downregulates MLCK kinase activity by decreasing the affinity of MLCK for $Ca^{2+}$-calmodulin. One of the two phosphorylated serine residues in the MLCK C-terminus is conserved in APEG-1 (Ser12), suggesting a regulatory site of APEG-1.

Telokin, originally purified as an acidic protein from turkey gizzard, is a protein that has the same peptide sequence as the carboxyl terminal domain of MLCKs. Its mRNA transcription initiates from a promoter that is located in one of the MLCK introns. Telokin transcription regulation is independent from that of MLCK despite having a sequence identical to the MLCK carboxyl terminal domain. Telokin has been proposed to be a calmodulin-binding protein (Holden, H. M., et al., 1992, J. Mol. Biol. 227:840–51), and it is expressed in almost every smooth muscle cell, except in the aortic smooth muscle cell. It is not expressed in any non-muscle cells (Gallagher, P. J., et al., supra).

When the APEG-1 polypeptide sequence was compared with those of MLCKs, there was a 33% identity at the amino acid level. However, several lines of evidence indicate that APEG-1 is not a rat homologue of a MLCK. First, peptide sequence comparison of APEG-1 to rat smooth muscle MLCK has only 24% identity, significantly less than the identity between APEG-1 and rabbit or chicken MLCKs. Second, the APEG-1 protein is predicted to be a basic protein, whereas the telokin protein is acidic. Third, rabbit telokin is not expressed in the aorta, in contrast to the specific expression pattern of APEG-1.

When the APEG-1 protein was analyzed to identify sequence motifs, several residues were identified as capable of being phosphorylated by protein kinase C and casein kinase-2. An arg-gly-asp (RGD) peptide sequence was found at position 90–92. This motif is present in many proteins involved in cell adhesion as well as signaling, and it interacts with its cell surface receptor, an integrin (Hynes, R. O., 1992, Cell 69:11–25, Ruoslahti, E., et al., 1987, Science 238:491–6). This observation suggests that APEG-1 protein plays role in cell signaling. The motif of two cysteine residues, four residues upstream and six residues downstream of the integrin-binding RGD sequence, are also conserved in the disintegrins, a family of platelet aggregation inhibitors found in snake venom (Blobel, C. P., et al., 1992, Curr. Opin. Cell. Biol. 4:760–5). The cysteine residue 6 residues downstream of the RGD sequence was also found to be present in the APEG-1 protein.

Northern and Genomic Southern Analyses of APEG-1

The APEG-1 full length CDNA was used as the probe to hybridize a 12-organ RNA Northern blot. In addition to the 1.3 kb message that appeared in the aorta, two other much larger messages (10–20 kb) were observed in skeletal muscle, esophagus, and heart. These two large messages were not initially identified by the APEG-1 3'-probe; therefore, it is likely the 5' sequence of APEG-1 CDNA hybridized to these new signals. To test this possibility further, three different probes from the 5', the middle, and the 3' portions of the APEG-1 cDNA sequence were used in Northern analysis (FIG. 9A). The result indicated that these 10–20 kb messages were recognized by the 5' but not by the 3' portion of the APEG-1 cDNA (FIGS. 9B–9D).

Southern blot analysis suggested that APEG-1 has a single copy in the rat genome, because there was only one 17.1 kb band in the EcoR I-digested rat genomic DNA (FIG. 10). This result further indicated that the large messages are unlikely to be products of other genes, unless these other genes are closely linked with APEG-1 without any intervening EcoR I sites. From the APEG-1 cDNA sequence two BamH I and one Hind III site were located (FIG. 9A). This correlated with the Southern analysis data in that three bands (18.7, 2.4, and 1.4 kb) in BamH I- and two bands (12.0 and 6.4 kb) in HindIII-digested genomic DNA were identified.

Cloning of the human APEG-1 cDNA

The APEG-1 cDNA probe was used to screen a human λgt11 aortic 5'-stretch cDNA library (Clontech). Four positive clones were purified, and the insert cDNA was sized by EcoRI digestion of the phage DNA and sequenced. The sequence of the human APEG-1 cDNA and the predicted amino acid sequence of the open reading frame encoding human APEG-1 are shown in FIG. 16 and FIG. 17, respectively.

The human APEG-1 cDNA can then be used to screen a genomic library to obtain the vascular cell-specific promoter sequences which regulate expression cell-specific expression of APEG-1.

Deposit

A plasmid containing DNA encoding rat APEG-1 (rat APEG-1 cDNA in pSP72 vector) has been deposited with the American Type Culture Collection (ATCC) under the terms of the Budapest Treaty on the International Recognition of the Deposit of Microorganisms for the Purpose of Patent Procedure on Mar. 3, 1995, and bears the accession number ATCC 97071. A plasmid containing DNA encoding human APEG-1 (human APEG-1 cDNA in pUC18 vector) was deposited with the American Type Culture Collection under the terms of the Budapest Treaty on Jun. 1, 1995, and bears the accession number ATCC 97180. Applicants' assignee, President and Fellows of Harvard College, acknowledges its duty to replace the deposit should the depository be unable to furnish a sample when requested due to the condition of the deposit before the end of the term of a patent issued hereon, and its responsibility to notify the ATCC of the issuance of such a patent, at which time the deposit will be made available to the public. Prior to that time, the deposit will be made available to the Commissioner of Patents under the terms of CFR §1.14 and 35 U.S.C. §112.

The absence of APEG-1 expression in primary culture cells

As discussed above, APEG-1 was initially identified in adventitia-removed aortic tissue, a tissue composed of smooth muscle cells and endothelial cells. To identify which of these two cell types express APEG-1 gene, total RNAs were harvested from primary cultured rat aortic smooth muscle cells and microvascular endothelial cells, both at the second passage, and these RNAs were used in Northern analysis. APEG-1 message was not detected in these cell types (FIG. 12). It is likely that the in vivo expression of APEG-1 was lost during in vitro cell culture. These data suggest that APEG-1 expression is strictly growth-regulated, such that its expression is downregulated when cells are growing in vitro, as has been observed with respect to gas1 gene expression (Sal, G. D., et al., 1992, Cell 70:595–607). Alternatively, since cultured smooth muscle cells are believed to exhibit a dedifferentiated phenotype (Pauly, R. R., et al., 1992, Circulation 86 (suppl III):III-68–73), APEG-1 may be expressed solely in fully differentiated endothelial or smooth muscle cells. APEG-1 expression in vivo was found to be vascular smooth muscle cell-specific, as shown in FIGS. 18A and 18B.

APEG-1 expression in the balloon injury animal model

Since APEG-1 gene expression in vitro is different from that in vivo, APEG-1 expression in vivo was studied. A balloon injury model of the rat carotid artery, which has been used extensively to study vascular smooth muscle cells in atherogenesis and vascular remodeling (Clowes, A. W., et al., 1983, Lab. Invest. 49(2):208–15, Clowes, A. W. et al., 1985, Circ. Res. 56:139–45), was used to study the expression modulation of APEG-1. In this animal model, the rat left carotid artery was injured by a 2F balloon catheter, intimal arterial endothelial cells completely removed, and the medial smooth muscle cell layer distended. After the carotid injury, formation of the neointima was initiated. This involves smooth muscle cells proliferating and migrating from the media. With this model, medial and neointimal smooth muscle cells reach their respective highest rates of proliferation two days and four days after the balloon injury, declining rapidly thereafter. The total number of smooth muscle cells approaches a maximum and remains constant after two weeks (Clowes, A. W. et al., 1985, supra).

Total RNAs from rat carotid arteries 2, 5, and 8 days after balloon injury were collected and used in Northern analysis with an APEG-1 cDNA probe. The results showed that APEG-1 is downregulated to 15%–20% of non-injured carotid arteries after 2 and 5 days; the expression recovered to 40% of control after 8 days (FIGS. 13A and 13B). These data suggest that APEG-1 expression is involved in the regulation of smooth muscle cell proliferation and/or migration, and expression has to be suppressed for either or both events to occur.

Production and purification of recombinant APEG-1

Recombinant APEG-1 was expressed as a fusion protein and purified by the pFLAG expression system (IBI) and subsequently injected into rabbit to produce antiserum. The rat APEG-1 cDNA was cloned into pFLAG-2 expression vector and used to transform the $E.\ coli$ BL21 cells. The transformed cells were grown and induced by IPTG (isopropyl-$\beta$-D-thio-galactopyroside) to express the vector-encoded fusion protein. The FLAG-APEG-1 fusion protein was then purified by anti-FLAG monoclonal antibody affinity chromatography from soluble cell extract, and the purity was monitored by both Coomassie blue staining (FIG. 14A) and Western analysis (FIG. 14B).

Methods of Diagnosis

The invention includes a method of detecting injury in a sample of vascular tissue. A depressed level of APEG-1 would predict a high degree of smooth muscle cell proliferation indicative of vascular tissue injury, e.g., restenosis. The diagnostic method of the invention is carried out by determining the level of APEG-1 gene expression in a tissue, e.g., a vascular biopsy obtained at atherectomy. The level of gene expression may be measured using methods known in the art, e.g., in situ hybridization, Northern blot analysis, or Western blot analysis using APEG-1-specific monoclonal or polyclonal antibodies. A decrease in the level of APEG-1 expression per cell in the test sample of tissue compared to the level per cell in uninjured control vascular tissue indicates the presence of a vascular injury in the test sample. For example, tissue obtained at atherectomy could be tested for APEG-1 expression, e.g., the level of APEG-1 transcript or protein. A depressed level of APEG-1 (compared to normal tissue) correlates with a high degree of smooth muscle cell proliferation indicating a high probability of restenosis. Such diagnostic procedures are useful to identify patients in need of therapeutic intervention to reduce or prevent restenosis.

Methods of Therapy

Upon vascular injury and other stimuli, cytokines and growth factors from activated vascular cells promote growth and migration of dedifferentiated vascular smooth muscle cells, resulting in atherosclerotic plaques and restenosis. Vascular injury such as that caused during surgery or balloon angioplasty can be treated by administering APEG-1 polypeptides or DNA encoding APEG-1 polypeptides operatively linked to appropriate expression control sequences. Other vascular conditions, e.g., atherosclerosis, transplant arteriosclerosis, and diabetes, which are characterized by a decrease in APEG-1 expression (FIG. 15) may be treated in a similar manner. APEG-1 polypeptide, DNA encoding an APEG-1 polypeptide, or compositions which stimulate the APEG-1 promoter may administered to increase the level of APEG-1 polypeptide in the injured vascular tissue and thus inhibit the growth of smooth muscle cells.

APEG-1 polypeptides may be administered to the patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 µmoles of the polypeptide of the invention would be administered per kg of body weight per day. The compositions of the invention are useful for parenteral administration, such as intravenous, subcutaneous, intramuscular, and intraperitoneal.

DNA (e.g., APEG-1-encoding DNA, vascular cell-specific promoters, and vectors) of the invention may be introduced into target cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others. For example, the DNA of the invention under the control of a strong constitutive promoter may be administered locally to a blood vessel during balloon angioplasty using an adenovirus delivery system.

A vascular cell-specific promoter may be used to direct the expression of APEG-1 or genes other than APEG-1. Thus, vascular diseases may be treated by administering a vascular cell-specific promoter of the invention operatively linked to a sequence encoding a heterologous polypeptide, e.g., an APEG-1 promoter linked to DNA encoding a growth inhibitor gene such as Rb, p21 or p18.

The DNA of the invention may be administered in a pharmaceutically acceptable carrier. The therapeutic composition may also include a gene delivery system as described above. Pharmaceutically acceptable carriers are biologically compatible vehicles which are suitable for administration to an animal e.g., physiological saline. A therapeutically effective amount is an amount of the nucleic acid of the invention which is capable of producing a medically desirable result in a treated animal.

As is well known in the medical arts, dosage for any given patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule. Determination of optimal dosage is well within the abilities of a pharmacologist of ordinary skill.

Drugs which stimulate the APEG-1 promoter may also be administered as described above to increase the level of expression APEG-1 in vascular tissue. Such drugs can be identified by contacting the APEG-1 promoter linked to a reporter gene with a candidate compound and measuring the level of expression of the reporter gene in the presence and absence of the compound. An increased level of expression in the presence of the compound compared to that in its absence indicates that the compound stimulates the APEG-1 promoter.

The invention also includes cells transfected with the DNA of the invention. Standard methods for transfecting cells with isolated nucleic acid are well known to those skilled in the art of molecular biology. Preferably, the cells are vascular smooth muscle cells, and they express an APEG-1 polypeptide of the invention encoded by the nucleic acid of the invention. Cells of the invention may be administered to an animal locally or systemically using intravenous, subcutaneous, intramuscular, and intraperitoneal delivery methods. Alternatively, prokaryotic or eukaryotic cells in culture can be transfected with the DNA of the invention operatively linked to expression control sequences appropriate for high-level expression in the cell. Such cells are useful for producing large amounts of the APEG-1 polypeptide, which can be purified and used, e.g., as a therapeutic or for raising anti-APEG-1 antibodies.

Other embodiments are within the following claims.

We claim:

1. A substantially pure DNA comprising a sequence encoding an aortic-preferentially-expressed gene-1 (APEG-1) polypeptide.

2. The DNA of claim 1, wherein said polypeptide is rat APEG-1.

3. The DNA of claim 1, wherein said polypeptide comprises the amino acid sequence of SEQ ID NO:3.

4. The DNA of claim 3, wherein said DNA comprises the sequence of SEQ ID NO:2.

5. The DNA of claim 1, wherein said DNA is operably linked to regulatory sequences for expression of said polypeptide, said regulatory sequences comprising a promoter.

6. The DNA of claim 5, wherein said promoter is vascular cell-specific.

7. A cell comprising the DNA of claim 1.

8. A method of making an APEG-1 polypeptide, comprising (a) providing the cell of claim 7, (b) culturing it under conditions permitting expression of said DNA, and (c) purifying APEG-1 polypeptide from the cell.

9. A substantially pure DNA comprising a nucleotide sequence encoding a polypeptide having the biological activity of an aortic-preferentially-expressed-gene-1 (APEG-1) polypeptide, wherein the polypeptide encoded by said nucleotide sequence comprises the sequence Arg-Gly-Asp.

10. A substantially pure DNA comprising (a) the sequence of SEQ ID NO:2 or (b) a degenerate variant thereof.

11. The DNA of claim 1, wherein said polypeptide is human APEG-1.

12. The DNA of claim 11, wherein said polypeptide comprises the amino acid sequence of SEQ ID NO:12.

13. The DNA of claim 11, wherein said DNA comprises the sequence of SEQ ID NO:11.

14. A substantially pure DNA comprising (a) the sequence of SEQ ID NO:11 or (b) a degenerate variant thereof.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 1308 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
GAATTCGGCA CGAGCAGAGA CTTAAGGAAG GTGCAGACGG GGTCCGTTTG CACAGCCTCA        60
GGGCGCGTCC ACATCCCCCT TCAGCAGCCC AATCACCTCT GATGAGGAGT ACCTGAGCCC       120
CCCAGAGGAG TTCCCAGAAC CTGGGGAGAC CTGGTCCCGA ACCCCTACCA TGAAGCCCAG       180
TCCCAGCCAG GATCGAGATT CCTCTGACTC TTCCTCCAAG GCACCCCCAA CCTTCAAGGT       240
CTCACTCATG GACCAATCAG TGAGAGAAGG TCAAGATGTC ATTATGAGCA TCCGCGTGCA       300
GGGGGAGCCC AAGCCTGTGG TCTCCTGGCT GAGGAATCGG CAGCCTGTGC GCCCAGACCA       360
GCGGCGCTTT GCAGAGGAGG CCGAGGGTGG GCTCTGCCGG TTGAGGATCC TGGCTGCTGA       420
GAGGGGAGAT GCTGGTTTCT ACACTTGCAA GGCGGTCAAC GAATATGGCG CTCGGCAGTG       480
TGAGGCCCGC CTGGAGGTCC GAGGCGAGTG AGCTCAGGGG GCCACCTGCG CTGCCCCGC        540
TACCCTCCGA GCTGCACCCC TGTCTCAGGC ACCTCCTGGA CCTCGCTGTG TTTCACTGCC       600
TCCTGCCCAC AGACCCAGCC GGCTCGCCGG CCCGGACATA GCCCATGCTC CCCTTCCCTC       660
CCTAGCCCAT ACAGCACCCT GGGGTAACCC ATCGGGCCCC TGTGGATCCT CCCTCCCCAA       720
GTGGATATGT GGCTGTGCAG ACCAGGAGGC CCCCAGAAGG ACTGAGTGTT GAGAAGGGAT       780
GGCCATGAGG TTGTGACAAG CTCCCCCCGT CCCCAGCCTC CATGTAGGGA GCATCCAGCG       840
AATGCATGTG CTATGCTGCT ACAGGCCACT GTCTGTCTCT CTGTCTGTCT GCCTGTGTGT       900
CTGTGACAGT CAGGGAAGAA AACCTTCGAG CTGAGGTGGG ATAAGACAGA ATAAGATGAT       960
AGAACACAGC ATCTGTGAGA TGCAGGGGCC CAGAGGGGCA GGCACAGTGG ATAGGAGACT      1020
CTCTGGGAAG GGTAGGGCAC TGACCATTGC AGAAATGGGT TTTAAATGGC ACAACATTTT      1080
TTATTCCACA TGAGACCAAA AGCTAGAGGT CTGGGATTAA GCCCTGACTG CTGGCAAGCT      1140
TAGGACCAAG TGGGGTACCC TTCTTCACAG ACACATCCGA CACGCTCTGT CTGGGAATGA      1200
GAGAGTAGCC AGACTGAGCA CAGGAGCAGG TCATAGTGGG ACTGGAGGTT TGGAAACACT      1260
ATTTCGTAGC TCAAATAAAG TCCAGTTTGT ACCCAAAAAA AAAAAAA                   1308
```

( 2 ) INFORMATION FOR SEQ ID NO:2:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

| | | | | | | |
|---|---|---|---|---|---|---|
| ATGAAGCCCA | GTCCCAGCCA | GGATCGAGAT | TCCTCTGACT | CTTCCTCCAA | GGCACCCCCA | 60 |
| ACCTTCAAGG | TCTCACTCAT | GGACCAATCA | GTGAGAAG | GTCAAGATGT | CATTATGAGC | 120 |
| ATCCGCGTGC | AGGGGGAGCC | CAAGCCTGTG | GTCTCCTGGC | TGAGGAATCG | GCAGCCTGTG | 180 |
| CGCCCAGACC | AGCGGCGCTT | TGCAGAGGAG | GCCGAGGGTG | GGCTCTGCCG | GTTGAGGATC | 240 |
| CTGGCTGCTG | AGAGGGGAGA | TGCTGGTTTC | TACACTTGCA | AGGCGGTCAA | CGAATATGGC | 300 |
| GCTCGGCAGT | GTGAGGCCCG | CCTGGAGGTC | CGAGGCGAGT | GA | | 342 |

( 2 ) INFORMATION FOR SEQ ID NO:3:

( i ) SEQUENCE CHARACTERISTICS:
        ( A ) LENGTH: 113 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:3:

| Met | Lys | Pro | Ser | Pro | Ser | Gln | Asp | Arg | Asp | Ser | Ser | Asp | Ser | Ser | Ser |
|---|---|---|---|---|---|---|---|---|---|---|---|---|---|---|---|
| 1 | | | | 5 | | | | | 10 | | | | | 15 | |
| Lys | Ala | Pro | Pro | Thr | Phe | Lys | Val | Ser | Leu | Met | Asp | Gln | Ser | Val | Arg |
| | | | 20 | | | | 25 | | | | | 30 | | | |
| Glu | Gly | Gln | Asp | Val | Ile | Met | Ser | Ile | Arg | Val | Gln | Gly | Glu | Pro | Lys |
| | | | 35 | | | | 40 | | | | | 45 | | | |
| Pro | Val | Val | Ser | Trp | Leu | Arg | Asn | Arg | Gln | Pro | Val | Arg | Pro | Asp | Gln |
| | 50 | | | | | 55 | | | | | 60 | | | | |
| Arg | Arg | Phe | Ala | Glu | Glu | Ala | Glu | Gly | Gly | Leu | Cys | Arg | Leu | Arg | Ile |
| 65 | | | | | 70 | | | | | 75 | | | | | 80 |
| Leu | Ala | Ala | Glu | Arg | Gly | Asp | Ala | Gly | Phe | Tyr | Thr | Cys | Lys | Ala | Val |
| | | | | 85 | | | | | 90 | | | | | 95 | |
| Asn | Glu | Tyr | Gly | Ala | Arg | Gln | Cys | Glu | Ala | Arg | Leu | Glu | Val | Arg | Gly |
| | | | 100 | | | | | 105 | | | | | 110 | | |
| Glu | | | | | | | | | | | | | | | |

( 2 ) INFORMATION FOR SEQ ID NO:4:

( i ) SEQUENCE CHARACTERISTICS:
        ( A ) LENGTH: 157 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:4:

| Met | Ala | Met | Ile | Ser | Gly | Met | Ser | Gly | Arg | Lys | Ala | Ser | Gly | Ser | Ser |
|---|---|---|---|---|---|---|---|---|---|---|---|---|---|---|---|
| 1 | | | | 5 | | | | | 10 | | | | | 15 | |
| Pro | Thr | Ser | Pro | Ile | Asn | Ala | Asp | Lys | Val | Glu | Asn | Glu | Asp | Ala | Phe |
| | | | 20 | | | | 25 | | | | | 30 | | | |
| Leu | Glu | Glu | Val | Ala | Glu | Glu | Lys | Pro | His | Val | Lys | Pro | Tyr | Phe | Thr |

```
                  35                      40                      45

Lys  Thr  Ile  Leu  Asp  Met  Glu  Val  Val  Glu  Gly  Ser  Ala  Ala  Arg  Phe
     50                      55                      60

Asp  Cys  Lys  Ile  Glu  Gly  Tyr  Pro  Asp  Pro  Glu  Val  Met  Trp  Tyr  Lys
65                      70                      75                           80

Asp  Asp  Gln  Pro  Val  Lys  Glu  Ser  Arg  His  Phe  Gln  Ile  Asp  Tyr  Asp
               85                           90                           95

Glu  Glu  Gly  Asn  Cys  Ser  Leu  Thr  Ile  Ser  Glu  Val  Cys  Gly  Asp  Asp
               100                     105                     110

Asp  Ala  Lys  Tyr  Thr  Cys  Lys  Ala  Val  Asn  Ser  Leu  Gly  Glu  Ala  Thr
               115                     120                     125

Cys  Thr  Ala  Glu  Leu  Leu  Val  Glu  Thr  Met  Gly  Lys  Glu  Gly  Glu  Gly
     130                     135                     140

Glu  Gly  Glu  Gly  Glu  Glu  Asp  Glu  Glu  Glu  Glu  Glu  Glu
145                     150                          155
```

( 2 ) INFORMATION FOR SEQ ID NO:5:

( i ) SEQUENCE CHARACTERISTICS:
        ( A ) LENGTH: 157 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:5:

```
Met  Ala  Met  Ile  Ser  Gly  Met  Ser  Gly  Arg  Lys  Ala  Ser  Gly  Ser  Ser
1                       5                       10                      15

Pro  Thr  Ser  Pro  Ile  Asn  Ala  Asp  Lys  Val  Glu  Asn  Glu  Asp  Ala  Phe
               20                      25                      30

Leu  Glu  Glu  Val  Ala  Glu  Glu  Lys  Pro  His  Val  Lys  Pro  Tyr  Phe  Thr
               35                      40                      45

Lys  Thr  Ile  Leu  Asp  Met  Glu  Val  Val  Glu  Gly  Ser  Ala  Ala  Arg  Phe
     50                      55                      60

Asp  Cys  Lys  Ile  Glu  Gly  Tyr  Pro  Asp  Pro  Glu  Val  Met  Trp  Tyr  Lys
65                      70                      75                           80

Asp  Asp  Gln  Pro  Val  Lys  Glu  Ser  Arg  His  Phe  Gln  Ile  Asp  Tyr  Asp
               85                           90                           95

Glu  Glu  Gly  Asn  Cys  Ser  Leu  Thr  Ile  Ser  Glu  Val  Cys  Gly  Asp  Asp
               100                     105                     110

Asp  Ala  Lys  Tyr  Thr  Cys  Lys  Ala  Val  Asn  Ser  Leu  Gly  Glu  Ala  Thr
               115                     120                     125

Cys  Thr  Ala  Glu  Leu  Leu  Val  Glu  Thr  Met  Gly  Lys  Glu  Gly  Glu  Gly
     130                     135                     140

Glu  Gly  Glu  Gly  Glu  Glu  Asp  Glu  Glu  Glu  Glu  Glu  Glu
145                     150                          155
```

( 2 ) INFORMATION FOR SEQ ID NO:6:

( i ) SEQUENCE CHARACTERISTICS:
        ( A ) LENGTH: 155 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:6:

```
Met  Ala  Met  Ile  Ser  Gly  Leu  Ser  Gly  Arg  Lys  Ser  Ser  Thr  Gly  Ser
```

|     | 1   |     |     |     | 5   |     |     |     |     | 10  |     |     |     |     | 15  |
|-----|-----|-----|-----|-----|-----|-----|-----|-----|-----|-----|-----|-----|-----|-----|-----|
| Pro | Thr | Ser | Pro<br>20 | Leu | Thr | Ala | Glu | Arg<br>25 | Leu | Glu | Thr | Glu | Glu<br>30 | Asp | Val |
| Ser | Gln | Ala<br>35 | Phe | Leu | Glu | Ala | Val<br>40 | Ala | Glu | Glu | Lys | Pro<br>45 | His | Val | Lys |
| Pro | Tyr<br>50 | Phe | Ser | Lys | Thr | Ile<br>55 | Arg | Asp | Leu | Glu | Val<br>60 | Val | Glu | Gly | Ser |
| Ala<br>65 | Ala | Arg | Phe | Asp | Cys<br>70 | Lys | Ile | Glu | Gly | Tyr<br>75 | Pro | Asp | Pro | Glu | Val<br>80 |
| Val | Trp | Phe | Lys | Asp<br>85 | Asp | Gln | Ser | Ile | Arg<br>90 | Glu | Ser | Arg | His | Phe<br>95 | Gln |
| Ile | Asp | Tyr | Asp<br>100 | Glu | Asp | Gly | Asn | Cys<br>105 | Ser | Leu | Ile | Ile | Ser<br>110 | Asp | Val |
| Cys | Gly | Asp<br>115 | Asp | Asp | Ala | Lys | Tyr<br>120 | Thr | Cys | Lys | Ala | Val<br>125 | Asn | Ser | Leu |
| Gly | Glu | Ala | Thr<br>130 | Cys | Thr | Ala | Glu<br>135 | Leu | Ile | Val | Glu<br>140 | Thr | Met | Glu | Glu |
| Gly<br>145 | Glu | Gly | Glu | Gly | Glu<br>150 | Glu | Glu | Glu | Glu | Glu<br>155 |     |     |     |     |     |

( 2 ) INFORMATION FOR SEQ ID NO:7:

( i ) SEQUENCE CHARACTERISTICS:
        ( A ) LENGTH: 155 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:7:

| Met<br>1 | Ala | Met | Ile | Ser<br>5 | Gly | Leu | Ser | Gly | Arg<br>10 | Lys | Ser | Ser | Thr | Gly<br>15 | Ser |
|-----|-----|-----|-----|-----|-----|-----|-----|-----|-----|-----|-----|-----|-----|-----|-----|
| Pro | Thr | Ser | Pro<br>20 | Leu | Thr | Ala | Glu | Arg<br>25 | Leu | Glu | Thr | Glu | Glu<br>30 | Asp | Val |
| Ser | Gln | Ala<br>35 | Phe | Leu | Glu | Ala | Val<br>40 | Ala | Glu | Glu | Lys | Pro<br>45 | His | Val | Lys |
| Pro | Tyr<br>50 | Phe | Ser | Lys | Thr | Ile<br>55 | Arg | Asp | Leu | Glu | Val<br>60 | Val | Glu | Gly | Ser |
| Ala<br>65 | Ala | Arg | Phe | Asp | Cys<br>70 | Lys | Ile | Glu | Gly | Tyr<br>75 | Pro | Asp | Pro | Glu | Val<br>80 |
| Val | Trp | Phe | Lys | Asp<br>85 | Asp | Gln | Ser | Ile | Arg<br>90 | Glu | Ser | Arg | His | Phe<br>95 | Gln |
| Ile | Asp | Tyr | Asp<br>100 | Glu | Asp | Gly | Asn | Cys<br>105 | Ser | Leu | Ile | Ile | Ser<br>110 | Asp | Val |
| Cys | Gly | Asp<br>115 | Asp | Asp | Ala | Lys | Tyr<br>120 | Thr | Cys | Lys | Ala | Val<br>125 | Asn | Ser | Leu |
| Gly | Glu | Ala | Thr<br>130 | Cys | Thr | Ala | Glu<br>135 | Leu | Ile | Val | Glu<br>140 | Thr | Met | Glu | Glu |
| Gly<br>145 | Glu | Gly | Glu | Gly | Glu<br>150 | Glu | Glu | Glu | Glu | Glu<br>155 |     |     |     |     |     |

( 2 ) INFORMATION FOR SEQ ID NO:8:

( i ) SEQUENCE CHARACTERISTICS:
        ( A ) LENGTH: 113 amino acids
        ( B ) TYPE: amino acid
        ( C ) STRANDEDNESS: Not Relevant
        ( D ) TOPOLOGY: linear (i i) MOLECULE TYPE: protein (x i) SEQUENCE DESCRIPTION: SEQ ID NO:8:

```
Met Lys Pro Ser Pro Ser Gln Asp Arg Asp Ser Ser Asp Ser Ser Ser
 1               5                   10                  15
Lys Ala Pro Pro Thr Phe Lys Val Ser Leu Met Asp Gln Ser Val Arg
             20                  25                  30
Glu Gly Gln Asp Val Ile Met Ser Ile Arg Val Gln Gly Glu Pro Lys
             35                  40                  45
Pro Val Val Ser Trp Leu Arg Asn Arg Gln Pro Val Arg Pro Asp Gln
         50                  55                  60
Arg Arg Phe Ala Glu Glu Ala Glu Gly Gly Leu Cys Arg Leu Arg Ile
 65                  70                  75                  80
Leu Ala Ala Glu Arg Gly Asp Ala Gly Phe Tyr Thr Cys Lys Ala Val
                 85                  90                  95
Asn Glu Tyr Gly Ala Arg Gln Cys Glu Ala Arg Leu Glu Val Arg Gly
             100                 105                 110
Glu
```

(2) INFORMATION FOR SEQ ID NO:9:

(i) SEQUENCE CHARACTERISTICS:
        (A) LENGTH: 35 amino acids
        (B) TYPE: amino acid
        (C) STRANDEDNESS: Not Relevant
        (D) TOPOLOGY: linear (i i) MOLECULE TYPE: protein (x i) SEQUENCE DESCRIPTION: SEQ ID NO:9:

```
Ser Arg Ser Ser Pro Pro Phe Asp Val Glu Gly Gly Pro Pro Val Trp
 1               5                  10                  15
Gln Glu Gly Cys Leu Ile Asp Tyr Thr Cys Lys Ala Val Asn Gly Cys
             20                  25                  30
Ala Leu Val
         35
```

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:10:

TTTTTTTTTT TTVG    14

(2) INFORMATION FOR SEQ ID NO:11:

(i) SEQUENCE CHARACTERISTICS:
        (A) LENGTH: 1225 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:11:

TCACCTCTGA TGAGGAATAC CTGAGCCCCC CAGAGGAGTT CCCAGAGCCT GGGGAGACCT    60

```
GGCCGCGAAC CCCCACCATG AAGCCCAGTC CCAGCCAGGA CCGCCGTTCT TCTGACACTG    120
GCTCCAAGGC ACCCCCCACC TTCAAGGTCT CACTTATGGA CCAGTCAGTA AGAGAAGGCC    180
AAGATGTCAT CATGAGCATC CGCGTGCAGG GGGAGCCCAA GCCTGTGGTC TCCTGGCTGA    240
GAAACCGCCA GCCCGTGCGC CCAGACCAGC GGCGCTTTGC GGAGGAGGCT GAGGGTGGGC    300
TGTGCCGGCT GCGGATCCTG GCTGCAGAGC GTGGCGATGC TGGTTTCTAC ACTTGCAAAG    360
CGGTCAATGA GTATGGTGCT CGGCAGTGCG AGGCCCGCTT GGAGGTCCGA GGCGAGTGAG    420
CTCAGGGGGC CACCTGCGCT CCCCCCGCTA CCCTCCGAGC CGCGCCCCTG TCTCAGGCAC    480
CTCTCGGACC TCGCTGTGTT TCACTGCCTC CTGCCCACAG ACCCAGGCCT GCCGGCCCGG    540
ACCCGTCCCA GCCTCCCCTC CCCACCCCAT GCAGCCCCCA GGGGGATAGC CCATGGGCCC    600
CTGTGGACAC TCCCTCCCCA AGTGGACACA TGGCTGTGCA GGCCAGGAGG CCCACAGATG    660
GACTGAGTGC TGGGAAGGGG CGGCTTCGAG GGGTATCAAC CCCCCGAGTC TCTCCCTGAA    720
GGGGAGCACC GGGCGAGTGC ATGTGCTACT GCTGCTACAG GCCTGTCTAT CTGTTTGTCT    780
GTCTGTGTGT CTGTGACAGT CAGGGAAGGA TGCCTCGGAG CTGAGGTGGG GTGAGACAGA    840
GTGGGAGAGA TTACGGCATG GCATGGAGGG GCCCAAGGAG CAGGGGCTGT TGACAAAGGC    900
CTTACCAGGA AGGGTTAGGA CACTGACCAT TCTAGAAATG GGTTTCGAAT GGCACAACAC    960
TTTCTATTTC ACAAAAGACC AAAAGCCAGA GGCCCCAGGC TCTGTGCTGA TGAACAGCCT   1020
GGCTGAGCCC TGGCCCTGGC AGGTTTAGGG CCCATTTGGG GCCCCTCCT TCTCTGTCAG    1080
GGCTGGGGTG CTCTGTCTGG GAATGAGGGA GTTAACCAAG TTTGGTGCAG GAGCAGGGC    1140
AGGGGGCCAC TGTAGTGAGC GTGGATGAAA TTTGGAACAC CTATTCTTAA TCAAATAAAG   1200
TCCAGTTTGT ACCTAAAAAA AAAAA                                        1225
```

(2) INFORMATION FOR SEQ ID NO:12:

(i) SEQUENCE CHARACTERISTICS:
      (A) LENGTH: 113 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:12:

```
Met Lys Pro Ser Pro Ser Gln Asp Arg Arg Ser Ser Asp Thr Gly Ser
 1               5                  10                  15
Lys Ala Pro Pro Thr Phe Lys Val Ser Leu Met Asp Gln Ser Val Arg
                20                  25                  30
Glu Gly Gln Asp Val Ile Met Ser Ile Arg Val Gln Gly Glu Pro Lys
            35                  40                  45
Pro Val Val Ser Trp Leu Arg Asn Arg Gln Pro Val Arg Pro Asp Gln
        50                  55                  60
Arg Arg Phe Ala Glu Glu Ala Glu Gly Gly Leu Cys Arg Leu Arg Ile
 65                  70                  75                  80
Leu Ala Ala Glu Arg Gly Asp Ala Gly Phe Tyr Thr Cys Lys Ala Val
                85                  90                  95
Asn Glu Tyr Gly Ala Arg Gln Cys Glu Ala Arg Leu Glu Val Arg Gly
                100                 105                 110
Glu
```